(12) United States Patent
Revets et al.

(10) Patent No.: US 6,936,263 B2
(45) Date of Patent: Aug. 30, 2005

(54) TH1 INDUCING NATURAL ADJUVANT FOR HETEROLOGOUS ANTIGENS

(75) Inventors: Hilde Revets, Meise (BE); Pierre Cornelis, Elsene (BE); Patrick De Baetselier, Berchem (BE)

(73) Assignee: Vlaams Interuniversitair Instituut voor Biotechnologie VZW, Zwjjnaarde (BE)

( * ) Notice: Subject to any disclaimer, the term of this patent is extended or adjusted under 35 U.S.C. 154(b) by 7 days.

(21) Appl. No.: 10/222,100

(22) Filed: Aug. 16, 2002

(65) Prior Publication Data

US 2003/0059439 A1 Mar. 27, 2003

Related U.S. Application Data

(63) Continuation of application No. PCT/EP01/01673, filed on Feb. 13, 2001.

(30) Foreign Application Priority Data

Feb. 18, 2000 (EP) .............................................. 00200589

(51) Int. Cl.[7] ........................ A61K 39/00; A61K 39/38; A61K 39/385; A61K 39/02; A61K 39/108; A61K 38/00; A61K 9/127; C12N 1/12; C12P 1/00; C12P 21/04

(52) U.S. Cl. ................. 424/260.1; 424/184.1; 424/185.1; 424/191.1; 424/193.1; 424/194.1; 424/197.11; 424/201.1; 424/203.1; 424/234.1; 424/275.1; 424/450; 424/823; 424/824; 424/825; 424/826; 424/828; 424/829; 424/269.1; 424/248.1; 435/41; 435/42; 435/69.1; 435/69.7; 435/252.1; 514/2; 514/8

(58) Field of Search .......................... 424/184.1, 185.1, 424/191.1, 193.1, 203.1, 194.1, 197.11, 201.1, 450, 234.1, 260.1, 269, 275.1, 248, 828, 829, 823–826, 269.1, 248.1, 190, 190.1; 435/41, 42, 69.1, 69.7, 252.1; 514/2, 8

(56) References Cited

U.S. PATENT DOCUMENTS

| 5,550,223 | A | * | 8/1996 | Duchene et al. ............ 536/23.7 |
| 5,955,090 | A | * | 9/1999 | Knapp et al. ............. 424/260.1 |
| 6,130,085 | A | * | 10/2000 | Hamers et al. ........... 435/320.1 |
| 6,228,371 | B1 | * | 5/2001 | Nano ....................... 424/248.1 |
| 6,300,102 | B1 | * | 10/2001 | Knapp et al. ............... 435/69.7 |
| 6,537,552 | B1 | * | 3/2003 | Minion et al. ............ 424/190.1 |
| 6,551,795 | B1 | * | 4/2003 | Rubenfield et al. ........ 435/69.1 |
| 6,607,731 | B1 | * | 8/2003 | Reed et al. ............... 424/269.1 |
| 6,613,337 | B1 | * | 9/2003 | Reed et al. ............... 424/269.1 |
| 6,638,517 | B2 | * | 10/2003 | Reed et al. ............... 424/269.1 |
| 2002/0198162 | A1 | * | 12/2002 | Punnonen et al. ............ 514/44 |
| 2003/0059439 | A1 | * | 3/2003 | Revels et al. ............. 424/191.1 |
| 2003/0162260 | A1 | * | 8/2003 | Minion et al. .............. 435/69.7 |

FOREIGN PATENT DOCUMENTS

WO    WO 01/60404 A2    8/2001

OTHER PUBLICATIONS

Duchene et al, J. Bacteriology, 1989, 171/8:4130–4137.*

Saint–Onge et al, J. General Microbiology, 1992, 138:733–741.*

Cornelius et al, Molecular Microbiology, 1989, 3/3:421–428.*

Stover et al, Nature, 2000, 406:959–964.*

Cote–Sierra et al, Gene, 1998, 221:25–34.*

International Search Report, International Application No. PCT/EP01/01673, dated Aug. 17, 2001 (3 pages).

International Preliminary Examination Report, International Application No. PCT/EP01/01673, dated Apr. 11, 2002 (8 pages).

* cited by examiner

*Primary Examiner*—Nita Minnifield
(74) *Attorney, Agent, or Firm*—TraskBritt

(57) ABSTRACT

The present invention relates to the use of the major OprI lipoprotein of *Pseudomonas aeruginosa* to elicit a Type-1 immune response towards a heterologous antigen. The invention relates specifically to the use of OprI—antigen fusion proteins to elicit the Type-1 response. More particularly, the present invention is directed to pharmaceutical formulations comprising OprI and/or OprI fusion proteins, optionally together with a suitable excipient, to stimulate the Th1 dependent, cellular immune response.

10 Claims, 17 Drawing Sheets

TH1 INDUCING NATURAL ADJUVANT FOR HETEROLOGOUS ANTIGENS

CROSS-REFERENCE TO RELATED APPLICATION

This patent application is a continuation of International Application Number PCT/EP01/01673, filed on Feb. 13, 2001 designating the United States of America, corresponding to International Publication No. WO 01/60404 (Aug. 23, 2001), published in English, the contents of the entirety of which is incorporated by this reference.

TECHNICAL FIELD

The present invention relates to the use of the major OprI lipoprotein of *Pseudomonas aeruginosa* to elicit a Type-1 immune response towards a heterologous antigen

BACKGROUND

Upon T-Cell Receptor (TCR) ligation, Th0 cells differentiate into distinct subsets characterized by their functions and cytokine production profiles (Mosmann and Coffinan, 1989). Th1 lymphocytes, characterized by the production of IL-2, IFN-γ and TNF-β, contribute to cellular immunity whereas Th2 lymphocytes, producing IL-4, IL-5 and IL-10, are mainly involved in humoral immunity. The generation of cell-mediated immunity against many infectious pathogens relies on the induction of the innate immune system, which in turn generates appropriate signals for adaptive immune responses (Fearon and Locksley, 1996). Bacterial lipoproteins are, among others, molecules that stimulate cells of the innate immune system to produce cytokines such as TNF-α (Radolf et al., 1991; Vidal et al., 1998) and IL-12 (Brightbill et al., 1999). Hereby, bacterial lipoproteins activate innate immune cells via Toll-like receptors (Brightbill et al., 1999; Aliprantis et al., 1999) and their signaling activity resides in the NH2-terminal triacylated lipopeptide region (Erdile et al., 1993; Weis et al., 1994). The potent capacity of bacterial lipoproteins and/or lipopeptides to induce the production of IL-12 (Brightbill et al., 1999), a key signal of the innate immune system, may in turn trigger the development of adaptive immune responses.

Numerous examples of the consequences on disease outcome of skewed Th1 to Th2 ratios have been reported. Polarized Th2 responses have been implicated in pathological situations, such as *Leishmania major* infection (Heinzel et al., 1991; Nabors et al., 1995), *tuberculosis* (TBC) (de Jong et al., 1997), human leprosy (Yamamura et al., 1991) and mycotic infections (Murphy et al., 1994). The contribution of Th1 cells relative to Th2 cells to the developing autoimmune response determines for a larger part whether or not this response leads to clinical disease (Racke et al., 1994; Racke et al., 1995; Leonard et al., 1995). In allergic asthma, a predominant Th2-type response has been noted (Vogel, 1997). Also the chronic autoimmune graft-versus-host disease, which develops after the administration of mismatched lymphoid cells, can be prevented by switching a Th2 response to a Th1 response through administration of IFN-γ at the time of cellular transfer (Donckier et aL, 1994).

Several methods have been proposed to modulate the Th1/Th2 response. WO9726883 describes the use of ribavirin3 to treat imbalances in lymphokine expression. WO9848805 discloses chemical compounds that suppress the Th2-type response and can be used for treating or preventing a disease caused by abnormal activation of a Th2-type immune response, such as asthma, allergic dermatitis, allergic rhinitis or systemic lupus erythematosus. However, those chemical compounds may have unwanted side effects. WO9921968 describes the use of macrophages in the function of antigen-presenting cells to redirect the balance of Th1/Th2 cell subsets during an immune response. Although the latter method is more specific, it is complicated because personalized immortalized macrophage clones should be made for each patient to be treated.

It has been demonstrated that bacterial lipoproteins may also be useful in modulating the Th1/Th2 immune response. The synthetic lipid moiety analogue of bacterial lipoproteins (i.e., the tripalmitoyl-s-glyceryl-cysteine or Pam3Cys) was reported to increase the immunogenicity of heterologous antigens (Bessler et al., 1985; Lex et al., 1986; Deres et al., 1989; BenMohamed et al., 1997). Lipopeptides derived from the outer surface lipoproteins of *Borrelia burgdorferi* were reported to induce Th1 phenotype development (Infante-Duarte and Kamradt, 1997). It has been reported that fusion proteins between the major OprI lipoprotein of *Pseudomonas aeruginosa* and heterologous peptides or proteins were found to be highly immunogenic as evidenced by the induction of strong humoral and cytotoxic T-cell responses without the need for adjuvants (PCT International Patent Publication WO9303762; Cornelis et al., 1996; Leitao et aL, 1998). There is no indication that OprI can modulate the immune response. Moreover, Ino et al. (1999) describes that OprI can act as a strong inducer of cytokines in mouse bone marrow cells. When purified OprI was added to mouse bone marrow cells, an induction of TNFα, IL-1a, IL-1b, IL-6 and granulocyte-macrophage colony stimulating was seen. However, IL-2, IFN-γ and TNF-β, typically seen in a Th1 response, were not detected. (Id.)

SUMMARY OF THE INVENTION

Surprisingly, it is demonstrated herein that the OprI-antigen fusion elicits a Type-1 immune response towards the heterologous antigen that is fused to OprI, even in the case where the antigen on its own does not induce a Th1 type response, or induces the Th1 response only to a limited extent. It is especially unexpected that this response is not only directed towards OprI itself, but also to the heterologous antigen, as is demonstrated by analysis of the antibody titers. The induction of the Type-1 immune response can be clearly allocated to the lipid tail of OprI. Therefore, one aspect of this invention is the use of OprI, or functional fragments thereof, as an adjuvant to obtain a Th1 type immune response against a heterologous antigen. A preferred embodiment of the invention is the use wherein OprI or a functional fragment thereof is fused to the heterologous antigen. One particular embodiment of the invention is the use wherein the antigen is gp63 of *Leishmania major* or a functional fragment thereof.

PCT International Publication WO 9504079 describes the use of OprI to expose proteins on the surface of host cells. It is unexpectedly demonstrated herein that host cells presenting a heterologous antigen fused to OprI, can stimulate the Th1 response towards the heterologous antigen in a similar way as if the purified OprI-antigen fusion protein is used. Therefore, another aspect of the invention is the use of a host cell expressing an OprI-heterologous antigen fusion protein to obtain a Th1 type response against the heterologous antigen.

Another aspect of the invention is the use of OprI and/or the use of an OprI-heterologous antigen fusion protein and/or the use of a host cell expressing an OprI-heterologous antigen fusion protein to treat a disease in which the natural Th1 response is insufficient, and/or the response is polarized towards a Th2 response. Such diseases are well known to the people skilled in the art and include, but are not limited to, Leishmaniasis, TBC, leprosy and mycotic infections, allergic asthma, and several autoimmune diseases such as chronic autoimmune graft-versus-host disease.

Still another aspect of the invention is a process for the manufacture of a pharmaceutical composition characterized in the use of OprI and/or OprI fused to a heterologous antigen and/or a host cell expressing an OprI-heterologous antigen fusion, according to the invention.

Still another aspect of the invention is a pharmaceutical composition to treat diseases in which the natural Th1 response is insufficient, comprising OprI and/or OprI fused to a heterologous antigen and/or a host cell expressing an OprI-heterologous antigen fusion protein, optionally together with a suitable excipient.

DETAILED DESCRIPTION OF THE INVENTION

Definitions

The following definitions are set forth to illustrate and define the meaning and scope of the various terms used to describe the invention herein:

Amino terminal amino acid means an amino acid of a peptide located proximate to the amino terminus of the peptide.

Suitable excipient means that the active ingredient can be formulated, for example, with the conventional generally non-toxic, well-known pharmaceutically acceptable carriers (e.g., sterile water, saline solution and other acceptable carriers) for making suitable pharmaceutical compositions. A person of skill in the art will recognize that a suitable excipient, examples of which are provided herein, is an art recognized term.

Functional fragment of OprI means any fragment that has still the adjuvant capacity and Th1 inducing ability. Preferentially, the functional fragment comprises at least 4 amino terminal amino acids of the sequence shown in SEQ ID NO:1, including the lipid modification, more preferentially at least 10 amino terminal amino acids of the sequence shown in SEQ ID NO:1, including the lipid modification, and most preferentially the functional fragments comprise the 57 amino terminal amino acids of the mature OprI protein, as shown in SEQ ID NO:1, including the lipid modification.

Functional fragment of an antigen means a part of the antigen that still has antigenic activity and contains at least one epitope.

Heterologous antigen means an antigen that has at least one epitope that differs from the epitopes of OprI.

Host cell means any host cell in which the OprI-heterologous antigen fusion protein can be expressed and wherein the antigen is presented on the surface of the host cell. Preferentially, the host cell is a bacterium, more preferentially, the host cell is a gram negative bacterium, even more preferentially, the host cell is *Escherichia coli*, *Alcaligenes eutrophus* or *Salmonella typhimurium*.

The invention is further explained by the use of the following illustrative Examples.

EXAMPLES

Materials and Methods

Mice

Female BALB/c, C57BL/6 and LPS-resistant C3H/HeJ mice of 6–8 weeks of age were obtained from Harlan Nederland (Horst, The Netherlands). C57BL/6 TNF-α knockout (TNF-α$^{-1-}$) mice were obtained from the National Institute of Animal Health, Tsukuba City, Japan (Taniguchi et al., 1997) and maintained in our animal facility.

Construction of pVUB3

Figure 1:
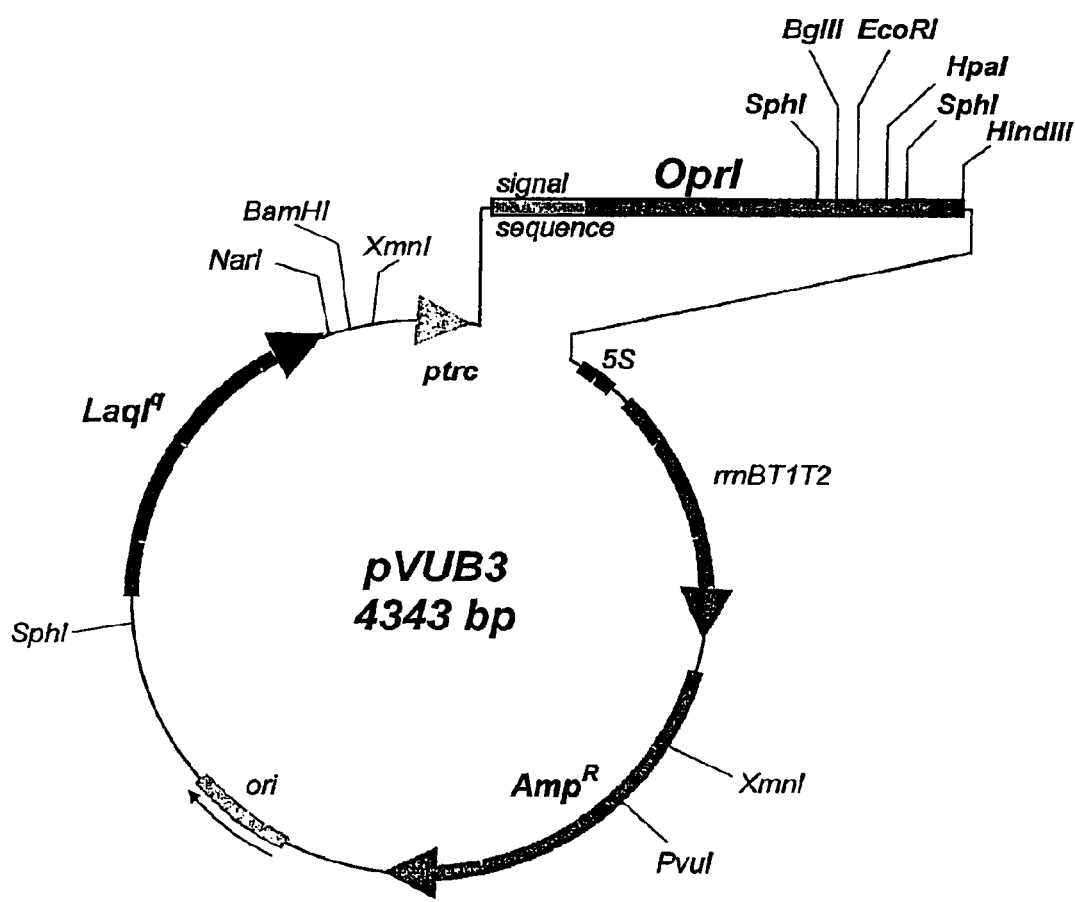
FIG. 1: Plasmid map of pVUB3.

The construction of the pVUB3 expression plasmid has been described in detail by Cote-Sierra et al. (1998). A plasmid map is depicted in FIG. 1.

Construction of the Expression Vector pCIMM2

Figure 2:
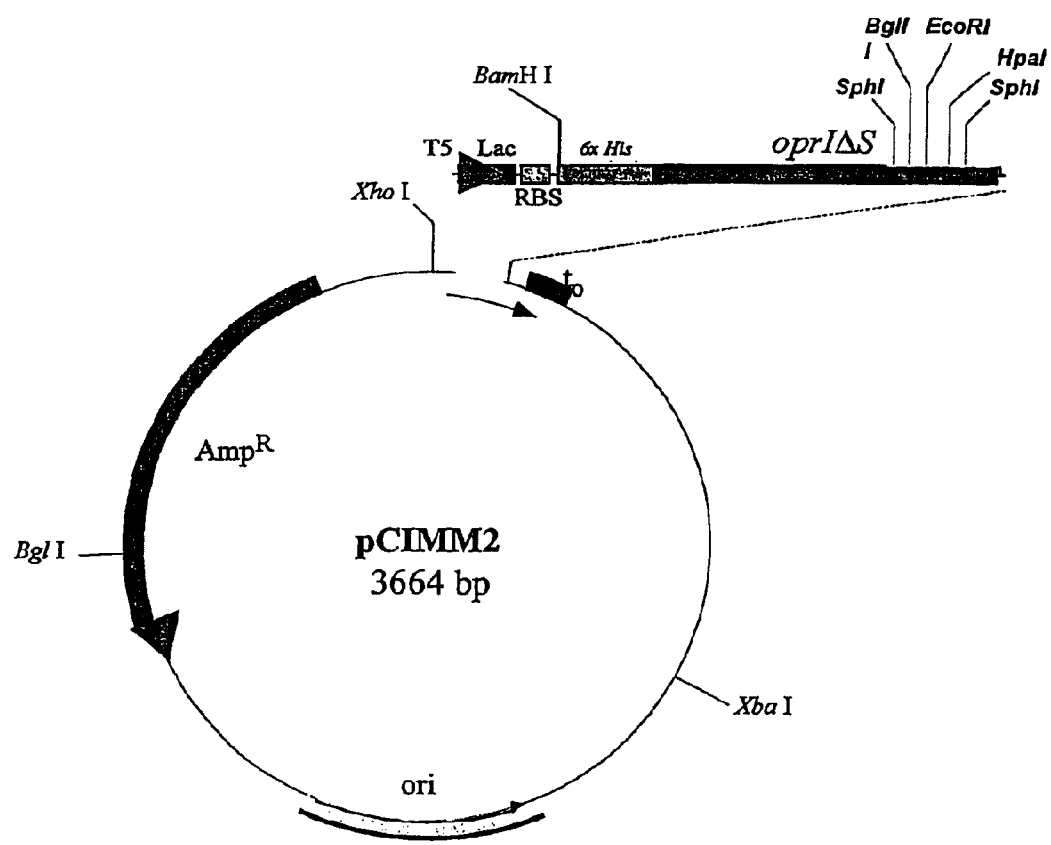
FIG. 2: Plasmid map of pCIMM2.

The *P. aeruginosa* mature OprI gene sequence contained in plasmid pVUB3 (Cote-Sierra et al., 1998) was amplified by PCR with the following primers 5'-GCGCGG-ATCCTGCAGCAGCCACTCCAAAGAAACCG-3' (SEQ ID NO:4) and 3'-CTTTTTCGGTCGGCGTTCATTA-TTCGAACGCG-5' (SEQ ID NO:5). Amplified DNA was purified, digested with BamHI and HindIII, and cloned downstream of a sequence encoding an oligo-histidine peptide of six residues in the expression vector pQE-8 (Qiagen GmbH, Germany), devoid of its EcoRI site. The resulting construct, pCIMM2, was transformed into JM109 competent cells. In pCIMM2, the OprIgene is devoid of its signal sequence and, consequently, cannot be transported to the bacterial outer membrane. As such, the protein will remain in the cytosol as a non-lipidated protein (NL-OprI). Due to the 6xHis tail at its 5' end, the protein can be purified by Immobilized Metal Affinity Chromatography (IMAC). In addition, the expression plasmid can be used for further subcloning of heterologous antigens into the NL-OprI sequence in order to create non-lipidated OprI/heterologous antigen fusion proteins. A plasmid map of pCIMM2 is depicted in FIG. 2.

Generation of Lipidated (L-OprI) Recombinant Antigens

Figure 3:
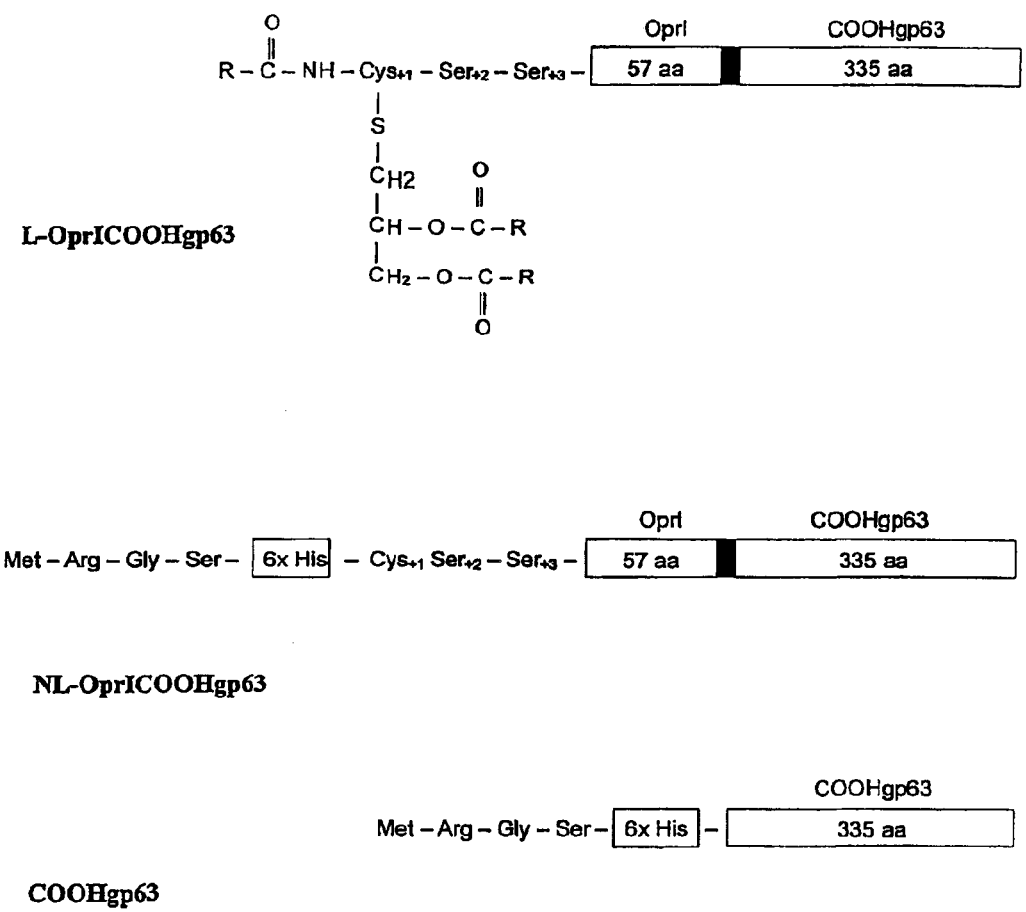
FIG. 3: Formulations of the three recombinant Gp63 preparations used in this study. L-OprICOOHgp63: lipidated OprI/COOHgp63 fusion protein; NL-OprICOOHgp63: non-lipidated OprI/COOHgp63 fusion protein; COOHgp63: 6xHis-tagged COOHgp63.

The generation of the lipidated L-OprICOOHgp63 fusion construct was described in detail previously (Cote-Sierra et al., 1998) (FIG. 3). The ligation mixture was subsequently transformed into a chemocompetent *E. coli* host using standard procedures.

Figure 9:
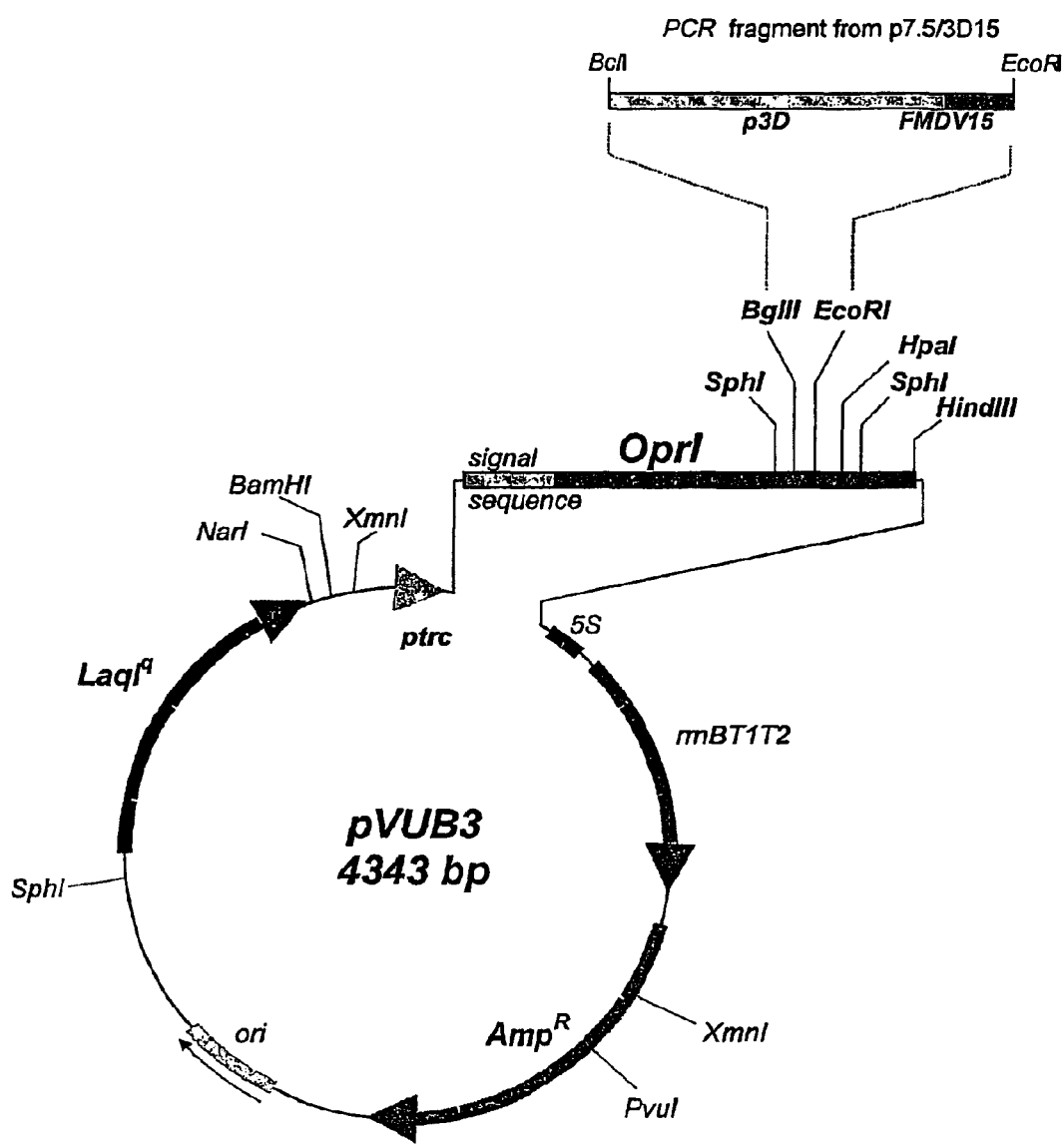
FIG. 9: Plasmid map of pVUB3:3D15.
Figure 10:
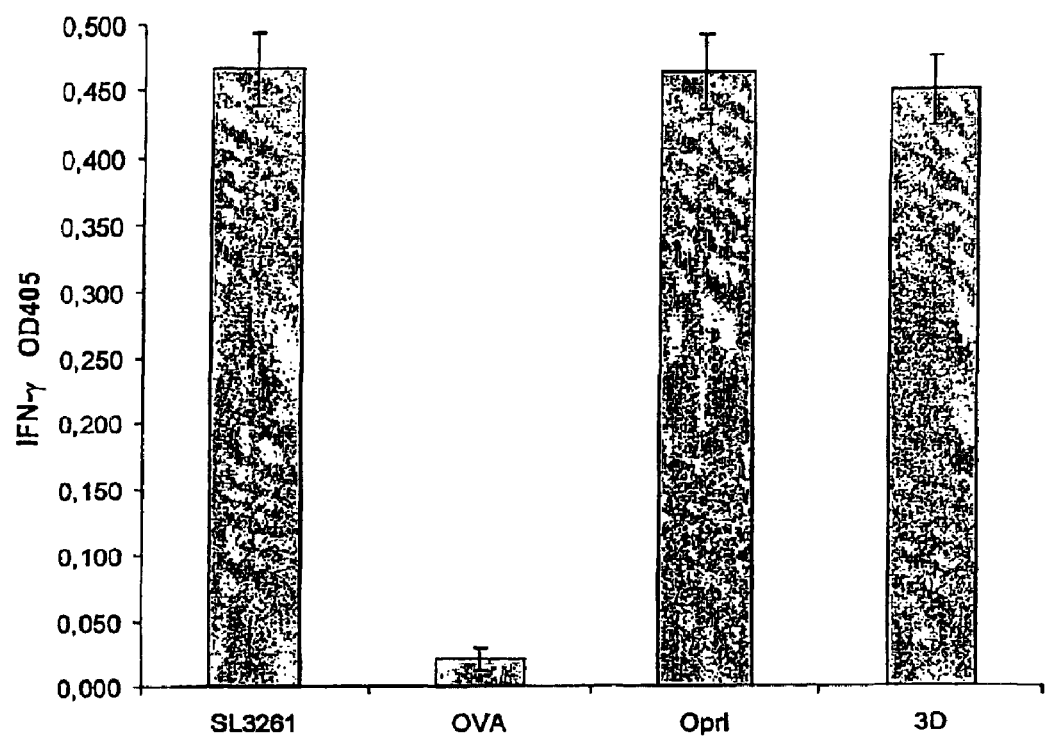
FIG. 10: IFN-γ (A) and IL-10 (B) production in spleen cells from mice immunized once with SL3261 (pVUB3:3D15). Splenic lymphocytes were restimulated with SL3261 lysate (SL3261), ovalbumin (OVA), non-lipidated OprI (NL-OprI) or 6× his-3D protein (3D).
Figure 10:
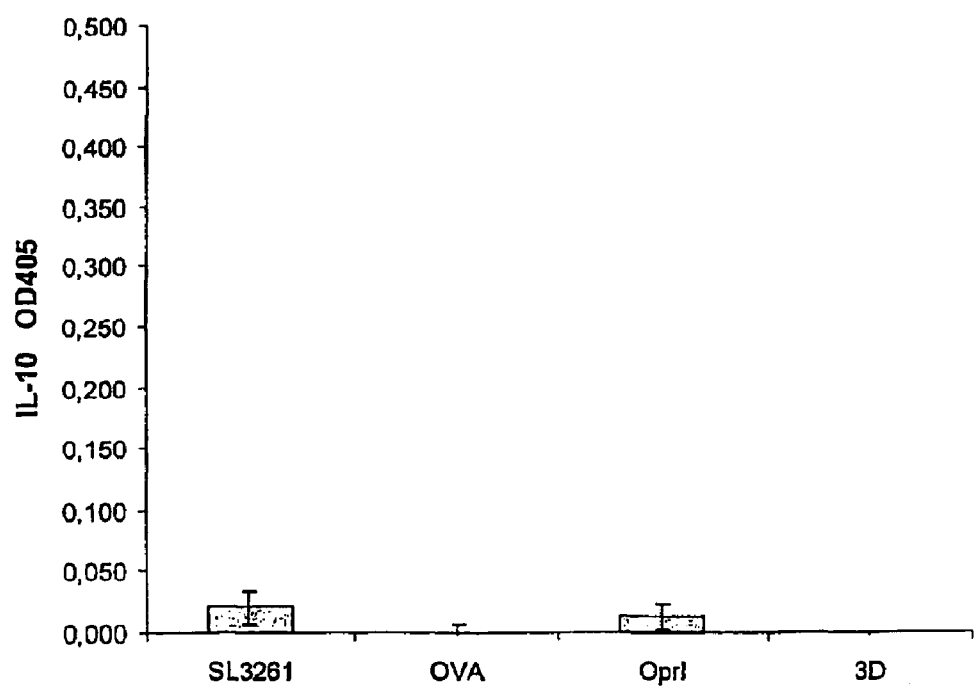
Figure 11:
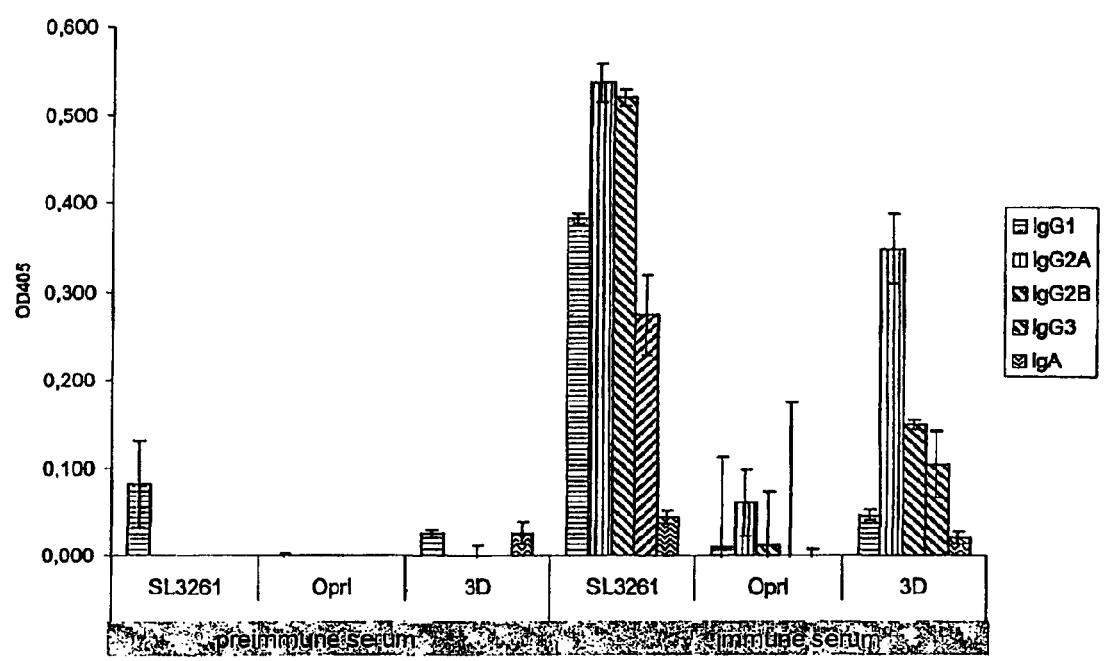
FIG. 11: Pre-immune and immune humoral isotype responses in mice immunized once with SL3261 (pVUB3:3D15). The abbreviations are the same as in FIG. 9.
Figure 12A:
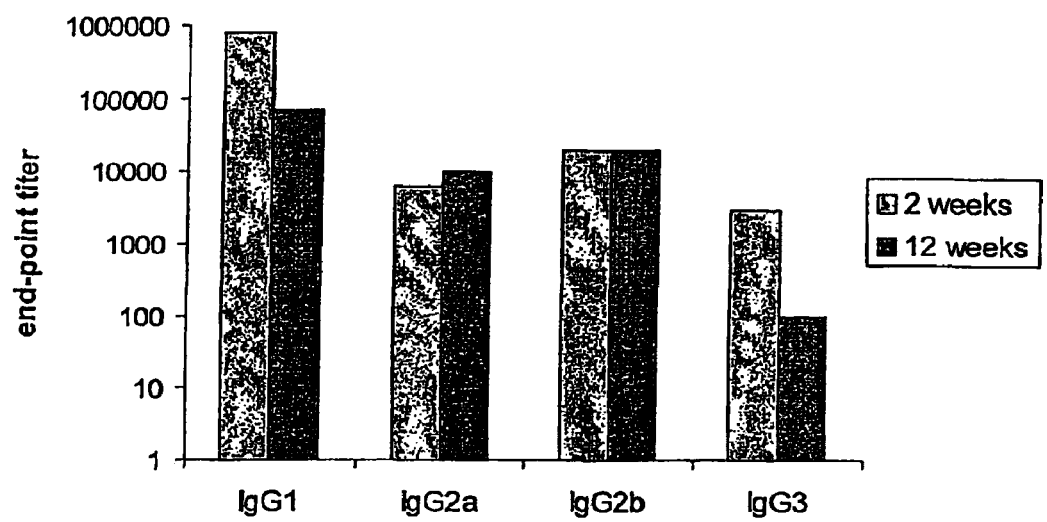
FIG. 12: (A) Antibody response measured in serum and (B) Production of IFN-γ in spleen cells from BALB/c mice, immunized 3 times at 10-day intervals, 2 and 12 weeks after immunization with L-OprICOOHgp63 (indicated as OprI-Cgp63).
Figure 12B:
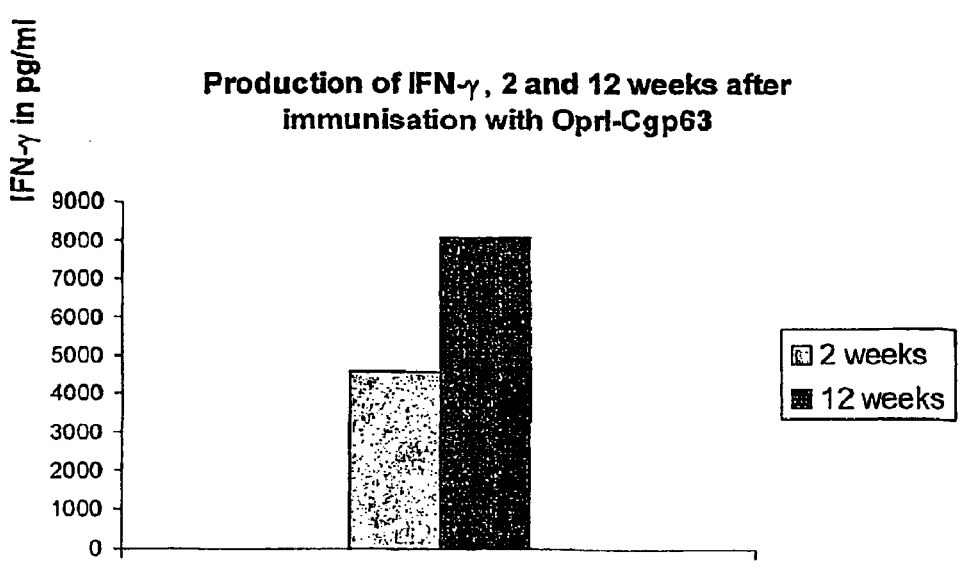
Figure 13A:
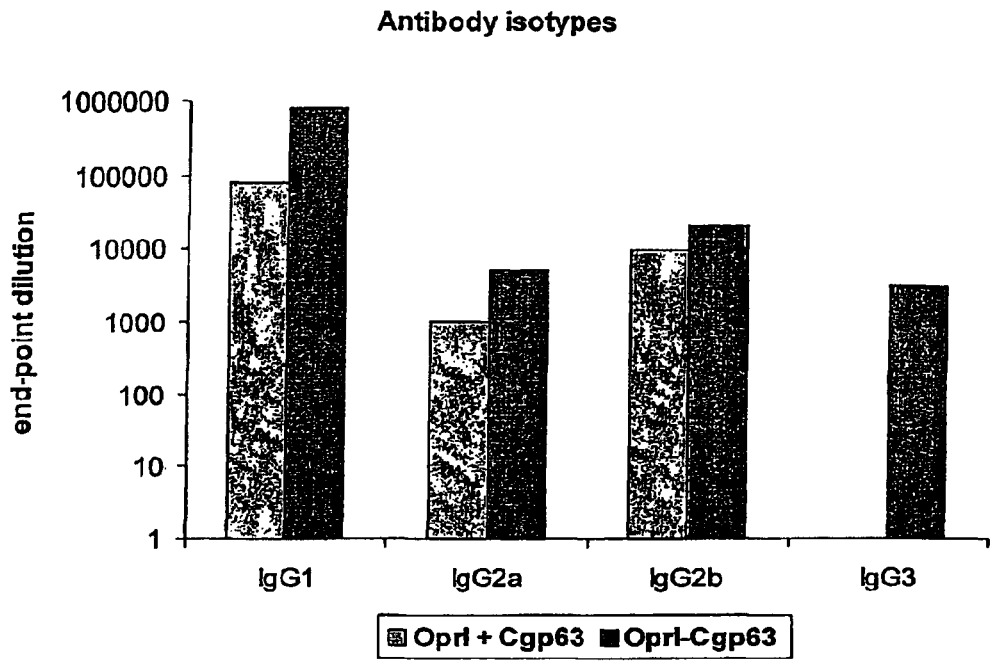
FIG. 13: (A) Antibody response measured in serum and (B) Production of IFN-γ in spleen cells from BALB/c mice, immunized 3 times at 10-day intervals, 2 and 12 weeks after immunization with either the L-OprICOOHgp63 fusion (indicated as OprI-Cgp63) or a mixture of L-OprI and COOHgp63 (indicated as OprI+Cgp63).
Figure 13B:
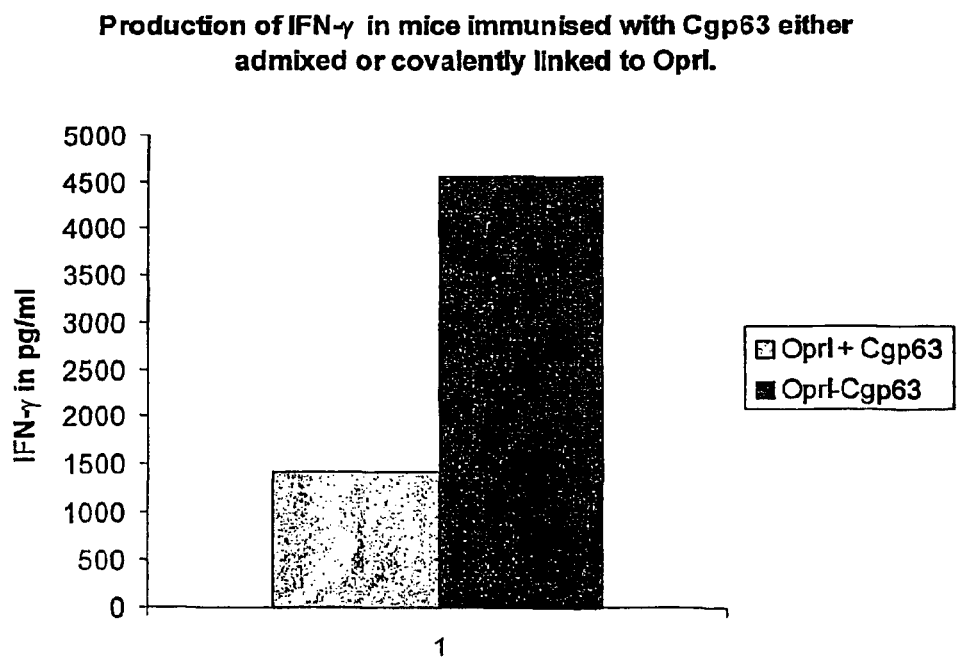

A lipidated L-OprI/3D-FMDVI5 fusion antigen (SEQ ID NO:3) was constructed as follows: the plasmid P7.5/3D15 containing the chimaeric 3D-FMDVI5 gene (a complex B-cell/T-cell construct consisting of the FMDV-15 peptide co-lineary linked with the T-ceil immunodominant non-structural protein 3D) was kindly provided by Dr. M. Parkhouse (Institute for Animal Health, Pirbright, U.K.). The chimaeric gene was amplified as a BclI-EcoRIPCR fragment and directionally cloned into the pVUB3 expression vector restricted with BglII-EcoRI (see, FIG. 9; SEQ ID. NO:2). The ligation mixture was subsequently transformed into a chemocompetent *E. coli* host using standard procedures.

Figure 15:
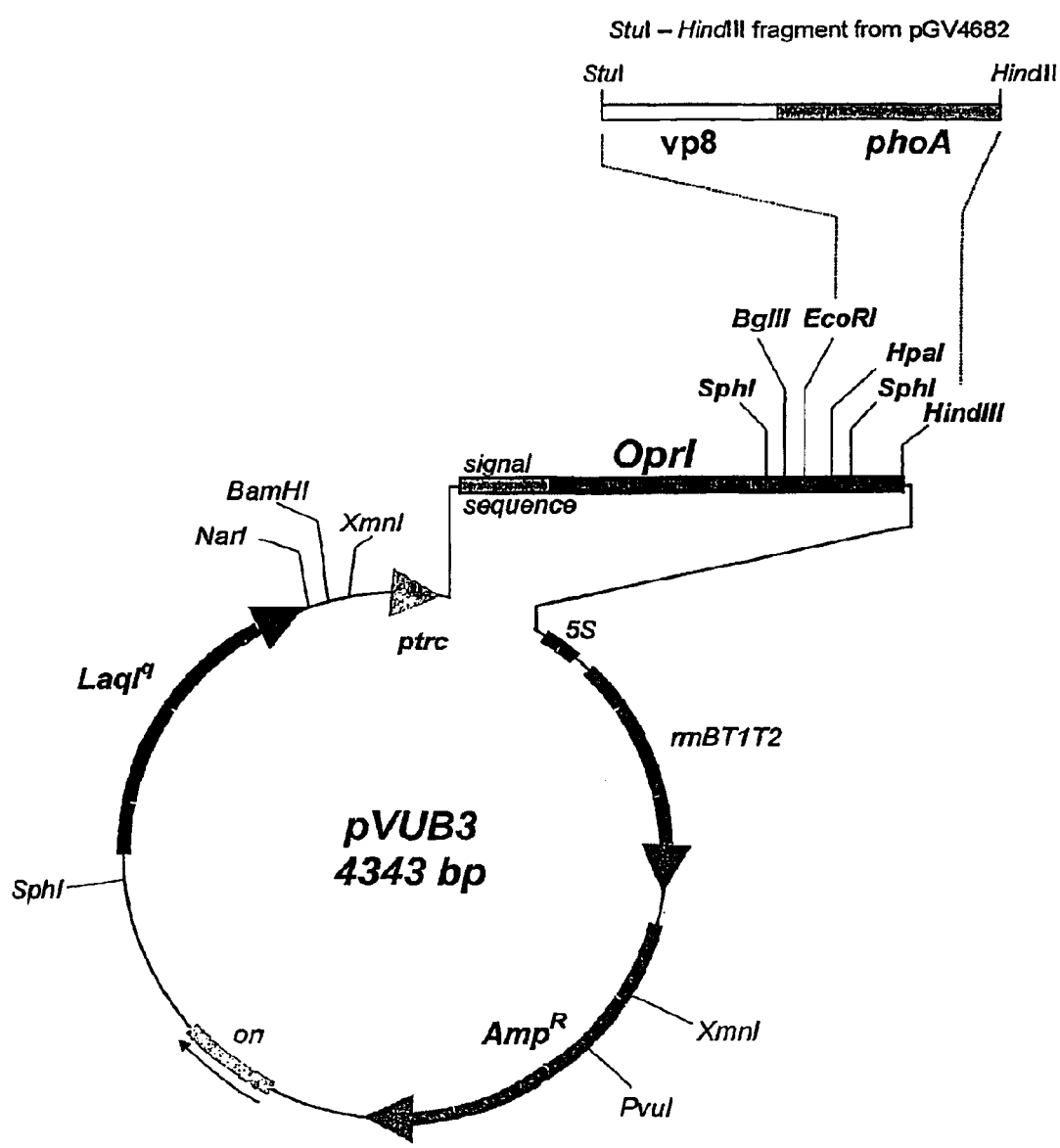
FIG. 15: plasmid map of pVUB3:VP8

The VP8 gene was amplified by PCR from the murine rotavirus strain EW (G3P17) and cloned into plasmid pGV4684 as fusion with phoA. Subsequently, the VP8-phoA fragment was ligated as a StuI-HindIII fragment into pVUB3, digested with EcoRI (filled in) and HindIII (FIG. 15). The ligation mixture was subsequently transformed into a chemocompetent *E. coli* host using standard procedures.

Generation of Non-Lipidated (NL-OprI) Recombinant Antigens

The recombinant vector producing the 6xHis-non-lipidated NL-OprICOOHgp63 protein (FIG. 3) was constructed by introducing the BglII-HindIII COOHgp63 DNA fragment (generated by digesting vector pVUB3:COOHgp63, Cote-Sierra et al., 1998) into the 6xHis-NL-OprI producing pCIMM2 plasmid (FIG. 2) using standard methods and the resulting plasmid was subsequently transformed into chemocompetent *E. coli* cells.

Construction of 6xHis-Tagged Antigens

The recombinant 6xHis-COOHgp63 protein (Indicated as COOHgp63; FIG. 3) was generated by directionally cloning the BglII-HindIII COOHgp63 DNA fragment (generated by digesting vector pVUB3:COOHgp63) into the expression vector pQE32 (Qiagen GmbH, Germany) digested with BamHI and HindIII.

The recombinant His-tagged FMDV 3D protein was generated by directionally cloning a BamHI-PstI FMDV-3D amplicon (generated by PCR amplification from the plasmid p7.5/3D15 (provided by Dr. M. Parkhouse, IAH, Pirbright, UK) using 3D-specific primers containing the BamHI or PstI restriction site coding sequence, respectively) into the expression vector pQE30 (Qiagen GmbH, Germany), restricted with the same enzymes. The resulting ligation mixture was subsequently transformed into chemocompetent *E. coli* cells using standard procedures.

Expression and Purification of Recombinant Antigens

Induction of L-OprI, L-OprI fusion proteins, 6xHis-NL-OprI, 6xHis-NL-OprI fusion proteins and 6xHis-tagged proteins with IPTG and preparation of outer membrane fractions was performed as described previously (Cornelis et al., 1996). OprI and OprI fusion proteins are purified from outer membrane fractions solubilized in a buffer containing 50 mM Tris-HCl pH 8.0, 0.6% SDS, 10 mM β-mercaptoethanol. The outer membrane proteins were loaded onto a preparative SDS-polyacrylamide column and purified by continuous elution electrophoresis using the Bio-Rad Model 491 Prep Cell (Bio-Rad Laboratories, Hercules, Calif., U.S.) according to the manufacturer's instruction. The 6xHis-tagged proteins, 6xHis-NL-OprI and 6xHis-NL-OprI fusion proteins were purified by affinity chromatography (IMAC) under denaturing conditions using the Ni-NTA superflow resin (Qiagen GmbH, Germany) or TALON Metal Affinity resin (Clontech, Palo Alto, Calif. US) and concentrated by using a VIVASPIN concentrator (VIVASCIENCE, Lincoln, UK), previously treated with 0.02% pluronic acid for 10 min (in the case of L-OprI and L-OprI fusion proteins). When necessary, IMAC-purified proteins were re-purified by continuous elution electrophoresis as mentioned above. Finally, proteins were subjected to two successive gel filtration chromatographies in the AKTA explorer (Amersham Pharmacia/Biotech, Sweden) using Superdex-75 HR10/30 (Pharmacia Biotech, Sweden) in order to remove LPS (Hoekstra et al., 1976), and eluted in a buffer containing 20 mM Tris-HCl, pH 8.0, 100 mM NaCl, 20 mM glycine and 0.01% SDS. Protein concentration was determined using the Bio-Rad DC Protein Assay (Bio-Rad Laboratories, Hercules, Calif. US). Lipopolysaccharide (LPS) in the protein suspension was determined by the Limulus Amebocyte Lysate Assay (Biowhittaker, Inc., Walkersville, Md., US).

Transformation of Recombinant Plasmid into Attenuated *Salmonella*

Figure 4A:
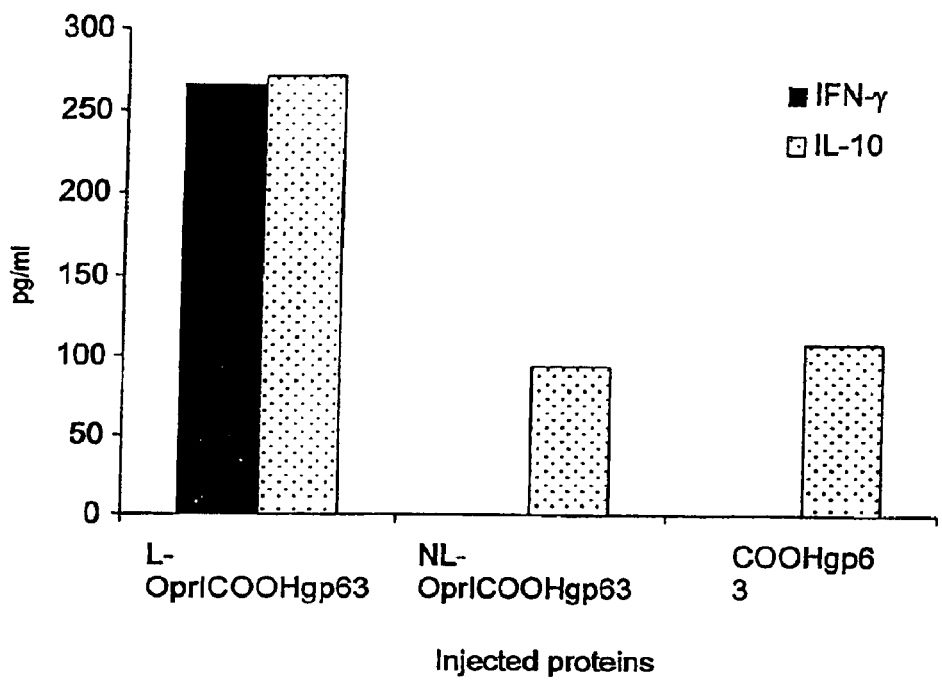
FIG. 4: Release of IFN-γ and IL-10 from lymph nodes of L-OprICOOHgp63, NL-OprICOOHgp63 and COOHgp63 immunized mice. Production of IFN-γ and IL-10 was quantified in the lymph nodes of BALB/c (A) and C57BL/6 (B) mice 7 days after immunization. Results show values of pooled sacral lymph nodes from five mice, representative of two similar experiments.
Figure 4B:
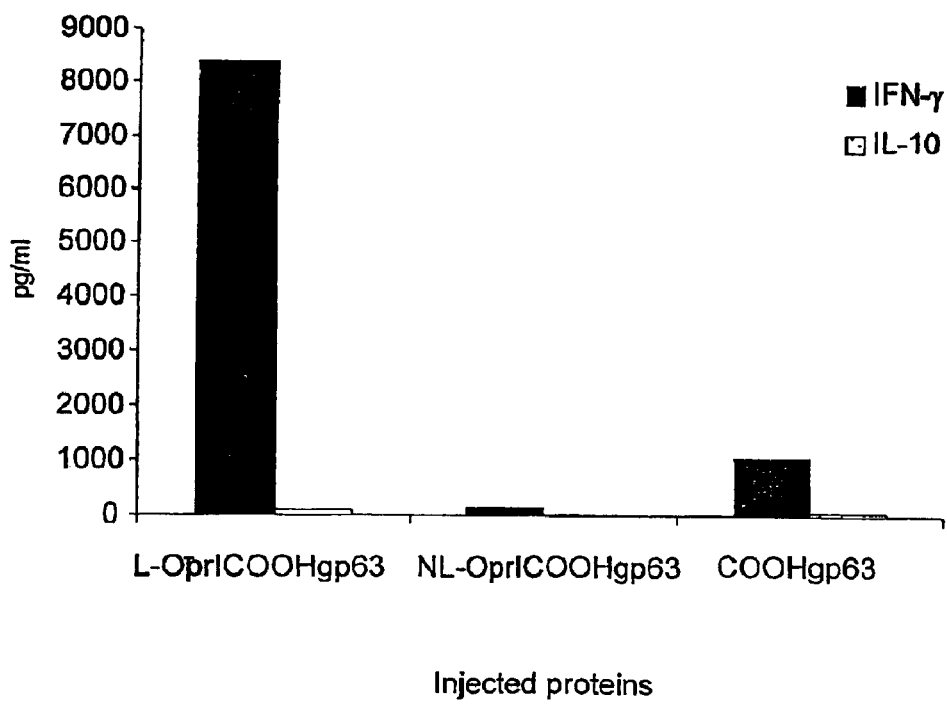
Figure 7A:
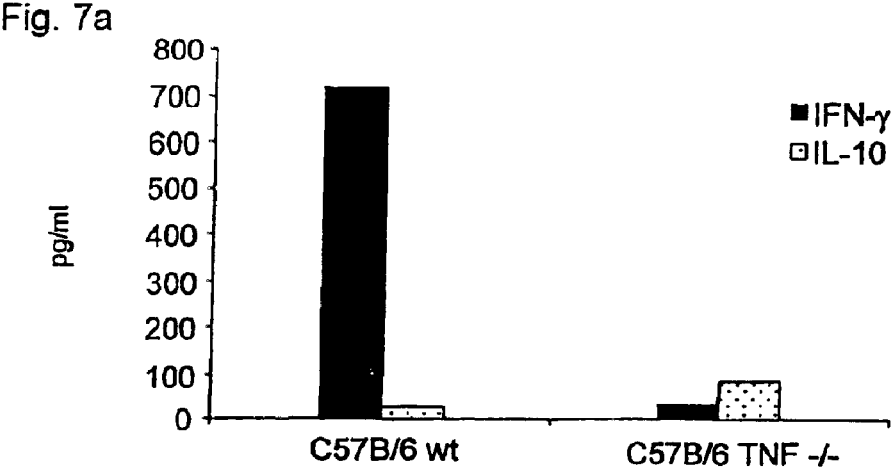
FIG. 7: The lipoprotein-induced Type-1 immune response is affected in TNF-α knockout mice (TNF-$\alpha^{-1-}$). IFN-γ and IL-10 production in sacral lymph node (A, C) and spleen (B, D) cells from mice immunized with one (A, B) or three doses (C, D) of L-OprICOOHgp63. IgG antibody titers against COOHgp63 in sera from BALB/c, C57BL/6 and C57BL/6 TNF-$\alpha^{-1-}$ mice, 10 days after mice received the third dose of L-OprICOOHgp63 (E). Results show end-point ELISA titers from pooled sera samples of five mice. Similar results were obtained in a second independent experiment.
Figure 7B:
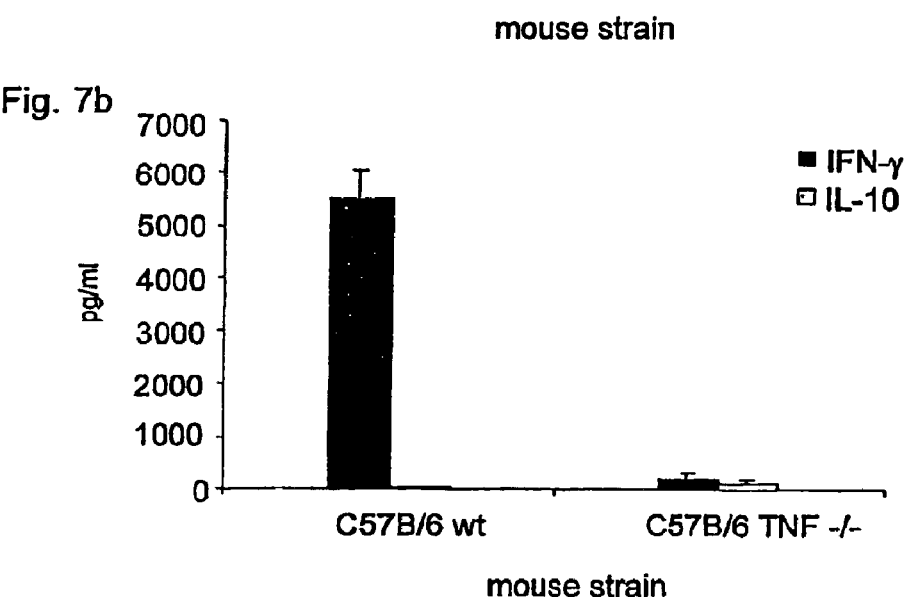
Figure 7C:
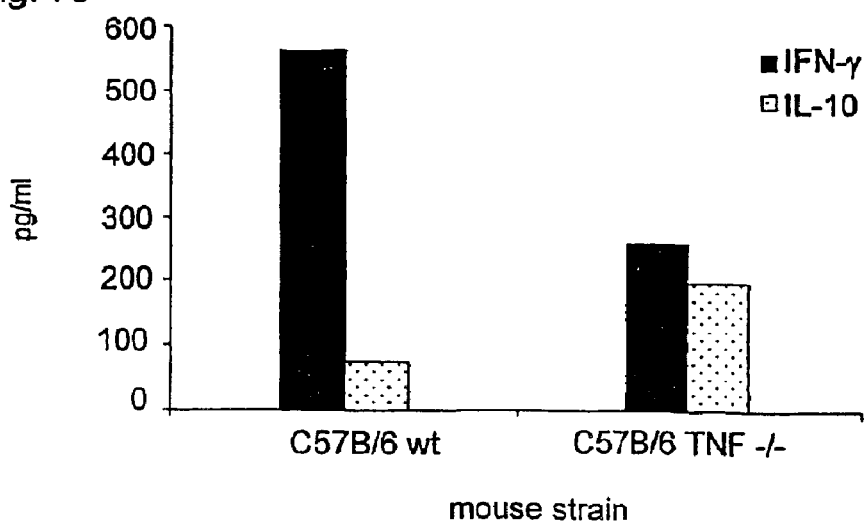
Figure 7D:
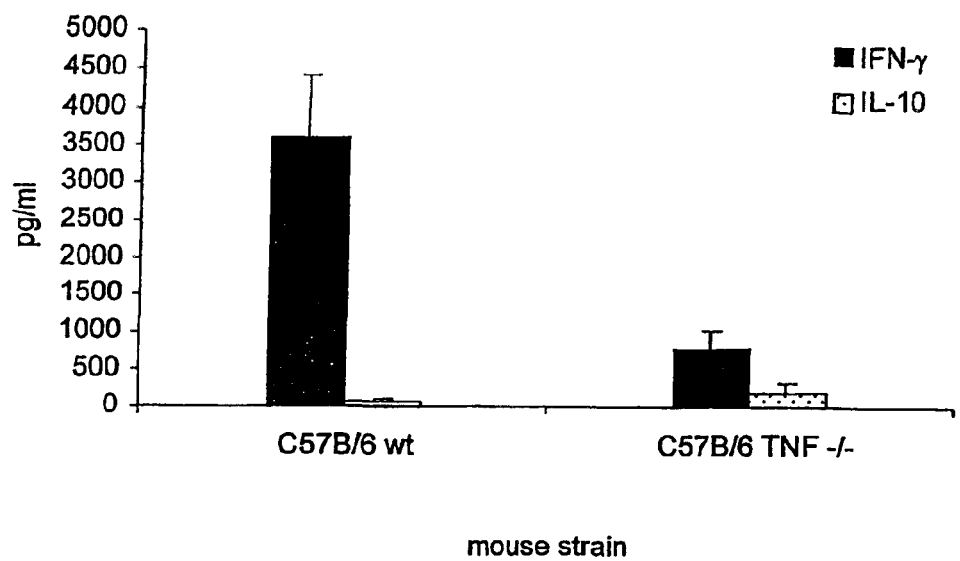

Plasmid DNA was transformed into the respective *Salmonella* strains by electroporation using standard procedures (2.5 kV, 400 Ω, 25 μF). After electroporation, the bacterial cells were grown for 2 h at 37° C. in LB medium. Aliquots of the transformation mix were grown on LB agar plates containing the appropriate antibiotic to select for recombinant bacteria.

Production of *Salmonella* Lysates

*Salmonella* cultures were grown overnight in LB medium at 37° C. The bacteria were pelleted, resuspended in PBS supplemented with protease inhibitors (Boehringer Mannheim) and subjected to 3 freeze-thaw cycles followed by sonication. After removing debris by centrifugation, the lysates were aliquoted and stored at −80° C. until use.

Production of *Salmonella* Live Oral Vaccines

Cultures of recombinant *Salmonellae* were statically grown overnight at 37° C. and used to seed fresh medium at a starting dilution of 1:50, and the subcultures were incubated at 37° C. until the $OD_{600}$ reached between 0.7–0.75. Expression of the recombinant L-OprI protein was then achieved by inducing the culture for 30 min with 1 mM IPTG. After induction, the bacteria were pelleted and resuspended to the appropriate cell density in PBS.

Immunizations with 6×His-Protein, L-OprI-, and NL-OprI Formulations

BALB/c, C57BL/6 or C57BL/6 TNF-$\alpha^{-1-}$ mice were subcutaneously immunized three times at 10-days intervals in the base of the tail with 1 μg of either 6×His-protein, L-OprI- or NL-OprI formulation. Preimmune sera were taken one daybefore the first immunization. Seven or 10 days after the first or third immunization respectively, mice were killed. Sera, spleens and draining lymph nodes (sacral lymph nodes) were taken to analyze the immune response.

Cytokine Assays

Homogeneous lymph node and spleen cell suspensions from individual mice were prepared in supplemented RPMI 1640 medium (10% fetal calf serum, penicillin—streptomycin 100 U and 100 μg/ml respectively, 2 mM L-glutamine, $5\times10^{-5}$ M 2-mercaptoethanol, 1×MEM amino acid solution and 1 mM sodium pyruvate). $2\times10^{6}$ cells were separately stimulated with or without the appropriate antigen at 37° C. in 24-well flat bottom tissue culture plates (Becton Dickinson, Franklin Lakes, N.J., USA). IFN-γ, IL-4, and IL-10 were determined in culture supernatants taken 24, 48,72 and 96 hours after priming. The cytokine levels were analyzed by a sandwich enzyme-linked immunosorbent assay (ELISA) in accordance to the supplier's instructions (Pharmingen, San Diego, Calif. USA). Data are represented as mean cytokine concentrations over 4 days.

Measurement of Antibody Titers

Immunoglobulin isotype titers in the preimmune and immune sera were measured by using ELISA (Southern Biotechnology Associates, Inc., Birmingham, Ala., USA). Briefly, 96-well Nunc-Immuno plates (Nalge Nunc International, DK) were coated with the appropriate antigen, and after exposure to diluted preimmune or immune sera, bound antibodies were detected by HRP-labeled goat anti-mouse IgG1, IgG2a, IgG2b, IgG3, IgA and IgM. ELISA titers were specified as the last dilution of the sample whose absorbance was above three fold the preimmune sera value.

Induction of TNF-α Production in Peritoneal Exudate Cells (PECs) After Antigen Stimulation PECs from LPS-resistant C3H/HeJ mice were harvested by washing the peritoneal cavity with 10 ml of ice-cold sucrose solution (0.34 M). The cells were washed in supplemented RPMI 1640 and left to adhere for 2 h. at 37° C. in 24-well flat bottom tissue culture plates (Becton Dickinson, Franklin Lakes, N.J., USA) at a concentration of $1\times10^{6}$ cells/ml. The peritoneal exudate cells were stimulated, or not, with recombinant murine IFN-γ (Life Technologies, Ltd., Paisley, Scotland, 100 U/ml) in the presence of L- and NL-OprICOOHgp63 or COOHgp63. After overnight incubation in a humidified atmosphere of 5% of $CO_2$, supernatants were collected to determine TNF-α concentrations by using the DuoSet ELISA development system (R&D Systems, Abingdon, UK).

*L. major* Challenge

Groups of 15 BALB/c mice were subcutaneously immunized three times with 1 μg of either L-OprICOOHgp63, NL-OprICOOHgp63 or COOHgp63 in buffer. A control group was immunized with the buffer only. Ten days after the third dose, mice were s.c. challenged with $10^{6}$ live virulent *L. major* promastigotes in the base of the tail. Progress of the disease was monitored weekly by scoring the lesion development.

CTL Assay

CTLs were derived from spleens of mice that had been immunized with the respective $OVA_{257-264}$ peptide (SIINFEKL; SEQ ID NO:6)/adjuvant or OVA protein/adjuvant formulations. Starting 10 days after the last immunization, CTLs were restimulated in vitro by incubating (1–2) $10^{8}$ spleen cells with $10^{7}$ irradiated (7000 rad) RMA-S/B7 cells loaded with $OVA_{257-264}$peptide (SIINFEKL; SEQ ID NO:6), in 50 ml RPMI complete medium, supplemented with 1 mM non-essential amino acids (Gibco), 1 mM sodium pyruvate (Gibco) and 20 μM 2-mercaptoethanol (Merck) for 5 days at 37° C. After isolation of blasts on a Ficoll-Paque gradient (Pharmacia Biotech, Uppsala, Sweden), the percentage specific lysis was determined in an $^{111}$In release assay (Kupiec-Weglinski et al., 1988), which is similar to the standard $^{51}$Cr-release assay. Briefly, target cells (RMA-S, RMA-S cells loaded with $OVA_{257-264}$peptide (SIINFEKL; SEQ ID NO:6)) labeled with $^{111}$In were incubated with CTL indifferent ratios for 4 h at 37° C. and release of $^{111}$In in the supernatant was measured. The percentage specific lysis was determined as [(release-spontaneous release)/(maximal release-spontaneous release)]. For maximal release, sodium dodecyl sulfate was added to the target cells (2% final concentration).

Example I

The Lipid Moiety of OprI-COOHgp63 Fusion Protein is Required for the Induction of Type-1 Immune Responses To evaluate the potential adjuvant capacity of the lipoprotein I of *P. aeruginosa* to heterologous proteins and the contribution of its lipid moiety to the immunogenicity of the chimeric OprI-COOHgp63 lipoprotein, three different recombinant proteins were produced: the lipidated L-OprICOOHgp63, the non-lipidated NL-OprICOOHgp63 and the COOHgp63 (FIG. 3). All three recombinant proteins contain the COOH-terminal domain of the glycoprotein Gp63 of *L. major*, which contains the host-protective T-cell epitopes (Yang et al., 1991). Mice (BALB/c, C57BL/6) were immunized subcutaneously once or three times with the recombinant proteins to respectively analyze the early cellular immune responses in the draining lymph nodes, and the secondary humoral immune responses, elicited against the heterologous COOHgp63 antigen. BALB/c is a highly susceptible mouse strain for *L. major* infection and an effective vaccine requires the induction of an IFN-γ-dependent Type-1 immune response (Reiner and Locksley, 1995; Milon et al., 1995). In vitro restimulation with the COOHgp63 of lymph node cells from BALB/c mice immunized once with either type of lipoprotein construct or COOHgp63 resulted in a clear induction of IL-10 secretion (FIG. 4A). In contrast, only lymph node cells from L-OprICOOHgp63-immunized BALB/c mice secreted IFN-γ (FIG. 4A). Likewise, in the C57BL/6 strain, only lymph node cells from animals immunized with L-OprICOOHgp63 produced very high levels of IFN-γ upon COOHgp63 restimulation (FIG. 4B). The induction of IFN-γ production was sustained after three immunizations as evidenced by the production of high IFN-γ levels in the spleen compartment, whereas the induction of IL-b production was completely abrogated (FIG. 7D). When IL-4 was measured in the same culture supernatants, a secretion pattern similar to IL-10 was seen. However, the levels of IL-4 production were either undetectable or much lower than the levels of IL-10.

Figure 5A:
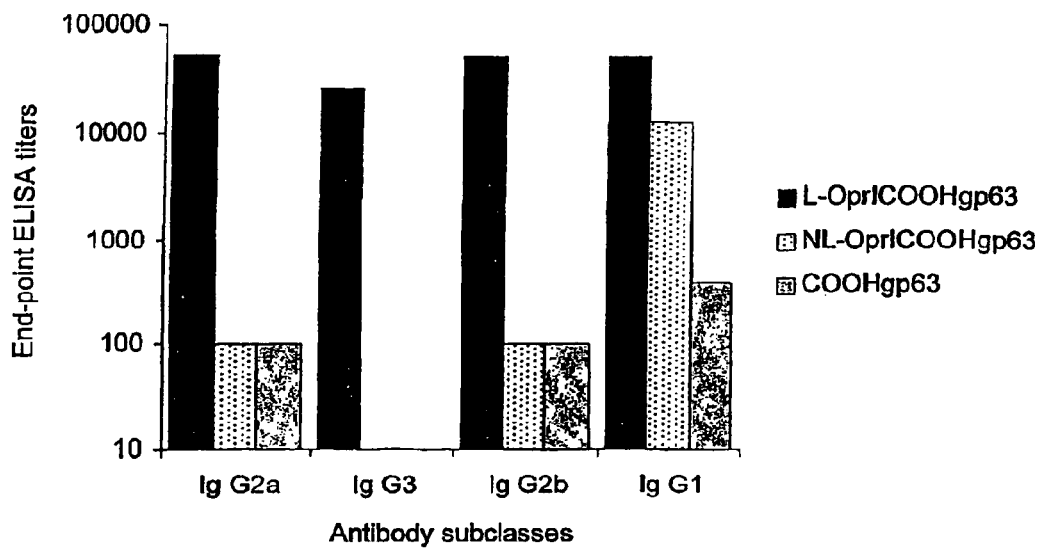
FIG. 5: Anti-Gp63 antibody responses in mice immunized with L-OprICOOHgp63, NL-OprICOOHgp63 or COOHgp63. IgG antibody titers against COOHgp63 in sera from BALB/c (A) and C57BL/6 (B) mice 10 days after mice received the third injection of the mentioned protein. Results of end-point ELISA titers are from pooled sera of five mice. The experiment was repeated twice and similar results were obtained.
Figure 5B:
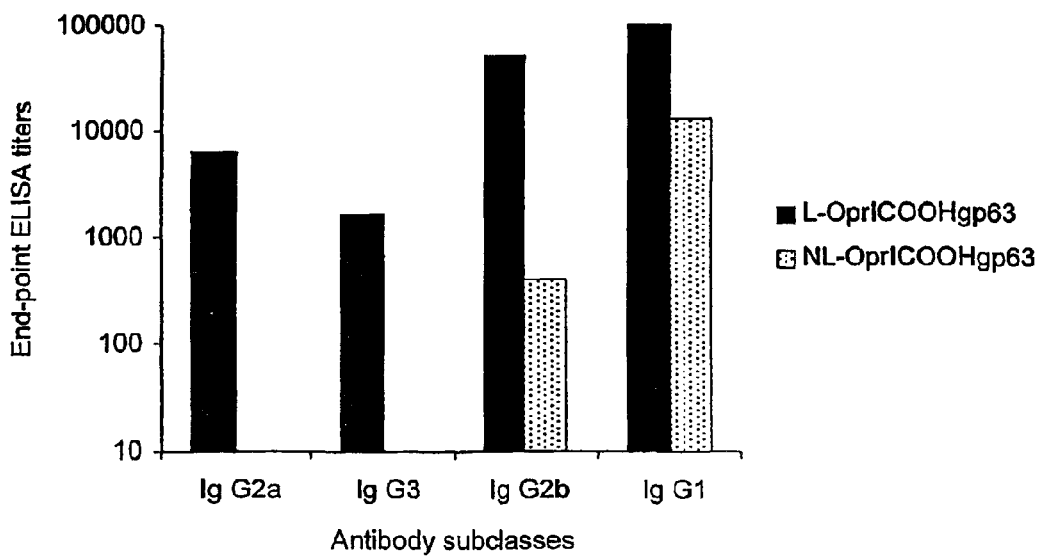

Antibody isotype responses against the COOHgp63 protein were also analyzed in immunized animals. As shown for BALB/c (FIG. 5A) and C57BL/6 mice (FIG. 5B), three immunizations with the lipidated OprI-COOHgp63 induced a significant production of COOHgp63-specific IgG2a, IgG3, IgG2b and IgG1 antibodies. In sharp contrast, the non-lipidated OprI-COOHgp63 and the COOHgp63 (the latter only shown for BALB/c mice) only induced significant levels of IgG1 anti-Gp63 antibodies and very low or undetectable levels of IgG2a, IgG3 and IgG2b in either mouse strain. There was no detectable IgA in the serum samples while the levels of IgM were marginal. Collectively, these immunization experiments demonstrate that the lipid tail of OprICOOHgp63 chimeric proteins elicit potent cellular (IFN-γ) and humoral (IgG2a and IgG3 antibodies) Type-1 immune responses.

Comparative analysis of lipidated OprICOOHgp63, the non-lipidated counterpart and COOHgp63 recombinant proteins in immunized mice demonstrated the crucial importance of the lipid tail of the *P. aeruginosa* lipoprotein I in inducing Type-1 immune responses against the heterologous antigen as evidenced by the cytokine pattern and profile of antibody subclass production. Indeed, a single immunization with the lipidated L-OprICOOHgp63 biased the T-cell response towards IFN-γ production, indicating a preferential induction of a Type-1 immune response. Besides the induction of IFN-γ producing cells, our results also demonstrate that the lipid tail of OprI potentiates the induction of humoral responses against a heterologous antigen since immunizations with L-OprICOOHgp63 increased or triggered IgG2a, IgG3 and IgG2b subclass responses against COOHgp63.

Example II

The Type-1 Inducing Potential of L-OprICOOHgp63 is TNF-α-Dependent

Figure 6:
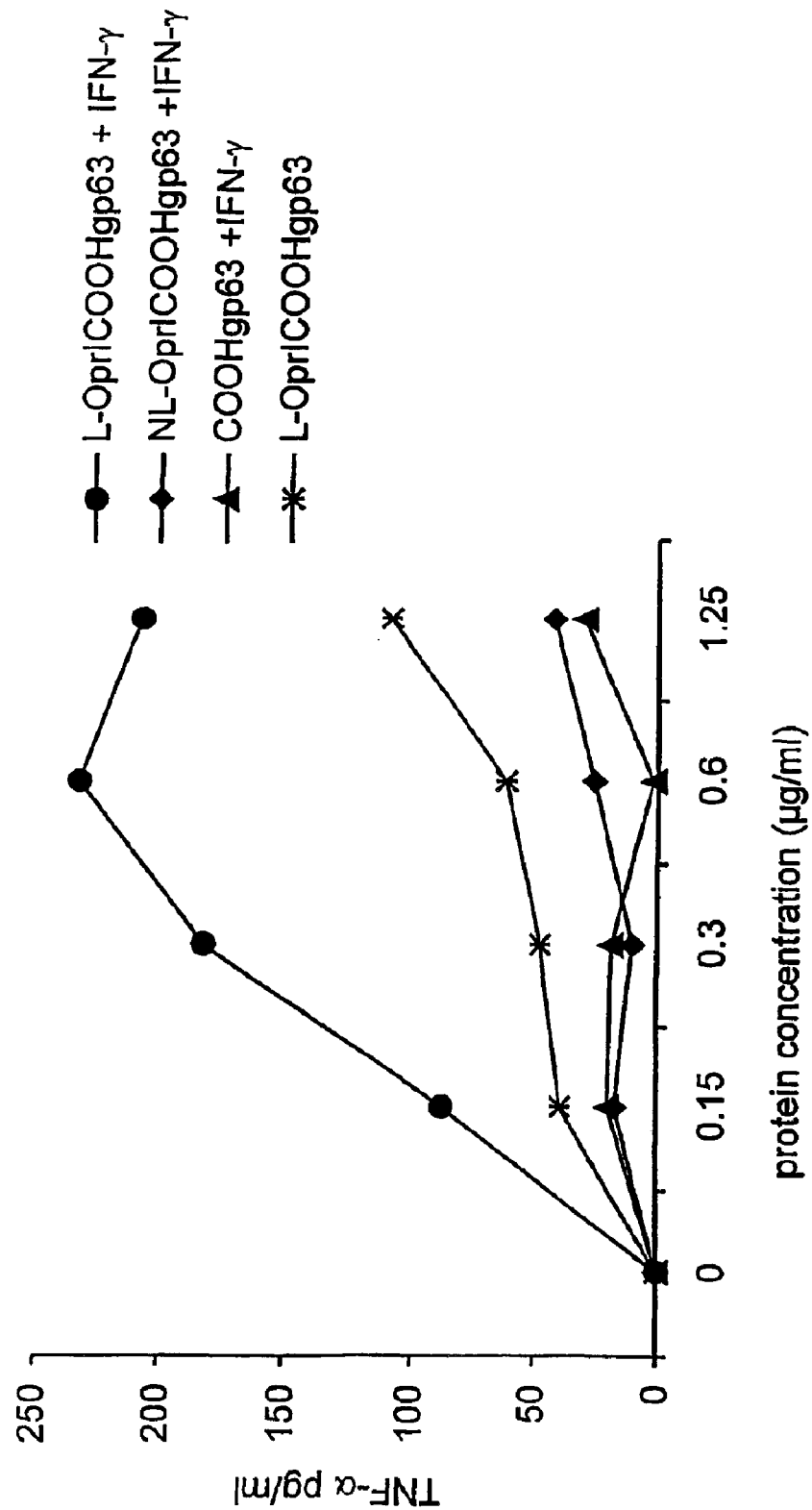
FIG. 6: The lipid tail of L-OprICOOHgp63 is required to induce TNF-α release by peritoneal macrophages either activated with 100 units/ml IFN-γ or without IFN-γ. The data are representative for two independent experiments.

TNF-α, secreted by lipoprotein-activated macrophages (Radolf et al., 1991; Vidal et al., 1998), has been suggested to be a key molecule, together with IL-12, in the induction of IFN-γ production and amplification of Type-1 immune responses (Butler et al., 1999; Tripp et al., 1993). Therefore, it was of interest to test whether (i) OprI-based lipoproteins induce TNF-α production by macrophages and (ii) TNF-α contribution to the Type-1 adjuvant activity of OprI. Macrophages (the plastic adherent fraction of peritoneal exudate cells (PEC), unactivated or activated with 100 units/ml IFN-γ) from endotoxin-resistant C3H/HeJ mice, were stimulated in vitro with either the lipidated COOHgp63, non-lipidated COOHgp63 or COOHgp63 antigen. As shown in FIG. 6, a dose-dependent induction of TNF-α in unprimed macrophages was recorded with the lipidated L-OprICOOHgp63.

Moreover, the TNF-α-inducing activity of L-OprICOOHgp63 was strongly increased in IFN-γ-primed macrophages (FIG. 6). In these experimental conditions, both the nonlipidated OprI-COOHgp63 and the COOHgp63 elicited marginal levels of TNF-α synthesis.

Figure 7E:
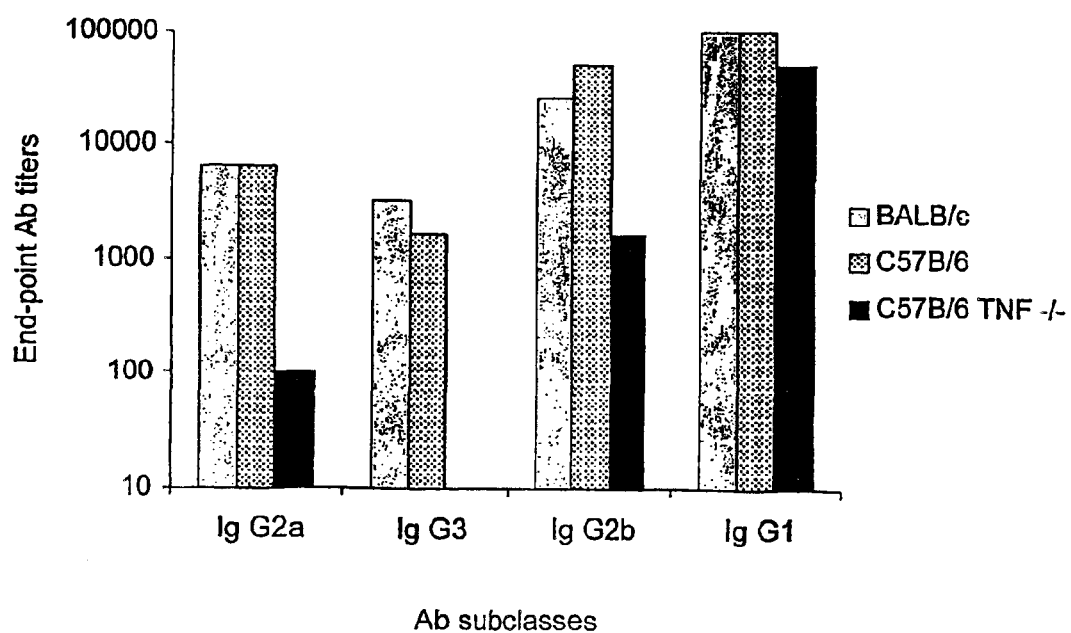

To test whether the TNF-α-inducing capacity of L-OprICOOHgp63 contributes to its Type-1 immune response-inducing potential, one and three immunizations with L-OprICOOHgp63 were performed in C57BL/6 TNF-$\alpha^{-1-}$ mice. As shown in FIG. 7, both early and late priming of COOHgp63-specific IFN-γ production was markedly reduced in the culture supernatants of draining lymph node (FIG. 7A) or spleen cells (FIG. 7B) from L-OprICOOHgp63-immunized TNF-$\alpha^{-1-}$ mice (single immunization) as compared to immunized C57BL/6 wild-type mice. Likewise, decreased Type-1 responses were also recorded in the culture supernatants of draining lymph node (FIG. 7C) and spleen cells (FIG. 7D) from TNF-$\alpha^{-1-}$ mice immunized three times with the antigen, and restimulated in vitro with COOHgp63. Analysis of the humoral responses elicited with L-OprI-COOHgp63 (after three immunizations) in BALB/c, C57BL/6 wild type and C57BL/6 TNF-$\alpha^{-1-}$ mice revealed that anti-COOHgp63 IgG3 and IgG2a responses were severely reduced in C57BL/6 TNF-$\alpha^{-1-}$ mice (FIG. 7E). In contrast, the magnitude of IgG1 and IgG2b subclass responses were respectively unaffected or less impaired in immunized C57BL/6 TNF-$\alpha^{-1-}$ mice as compared to wild type C57BL/6 and BALB/c mice. Altogether, these data suggest that the Type-1 immune response elicited by OprI is strongly TNF-α-dependent.

The capacity of L-OprICOOHgp63 to instruct acquired immune responses may reflect its potential to trigger innate immune cells. Corroborating other reports that bacterial lipoproteins are potent inducers of TNF-α production (Radolf et al., 1991; Vidal et al., 1998), our results show that only L-OprICOOHgp63 was capable to stimulate significant TNF-α production by either naive or IFN-γ-primed macrophages. Local production of TNF-α may in turn signal the development of Type-1 acquired immune responses. Indeed, this cytokine was documented to induce the expression of B7-like costimulatory signals (Swallow et al., 1999), IFN-γ production by T-cells (Butler et al., 1999; Darji et al., 1996) and NK cells (Tripp et al., 1993) and Type-1 antibody subclass responses (i.e., IgG2a) (Pasparakis et al., 1996). The involvement of TNF-α in the genesis and/or progression of cellular and humoral Type-1 acquired immune responses to leishmanial antigens is herein further substantiated since both Type-1 cytokine (IFN-γ) and humoral subclass (IgG3 and IgG2a) responses against the heterologous antigen were severely compromised in L-OprICOOHgp63-immunized TNF-$\alpha^{-1-}$ mice. It should be emphasized that CFA-aided immunization did not reveal similar defects in TNF-$\alpha^{-1-}$ mice. Hence, the defective induction of Type-1 responses recorded in L-OprICOOHgp63-immunized TNF-$\alpha^{-/-}$ mice most probably reflects the TNF-$\alpha$-inducing potential of OprI by virtue of its lipid tail. According to our in vivo results, TNF-$\alpha$ can be considered as a component of the innate immune system which, synergistically with or alternatively to IL-12, bridges the gap between innate and acquired immunity. Finally, since the TNF-$\alpha$-inducing capacity of OprI is strongly increased upon macrophage-priming with IFN-$\gamma$, TNF-$\alpha$-mediated induction of IFN-$\gamma$ production by OprI-based vaccines may further amplify ongoing or subsequent OprI-elicited immune responses.

Example III

Figure 8:
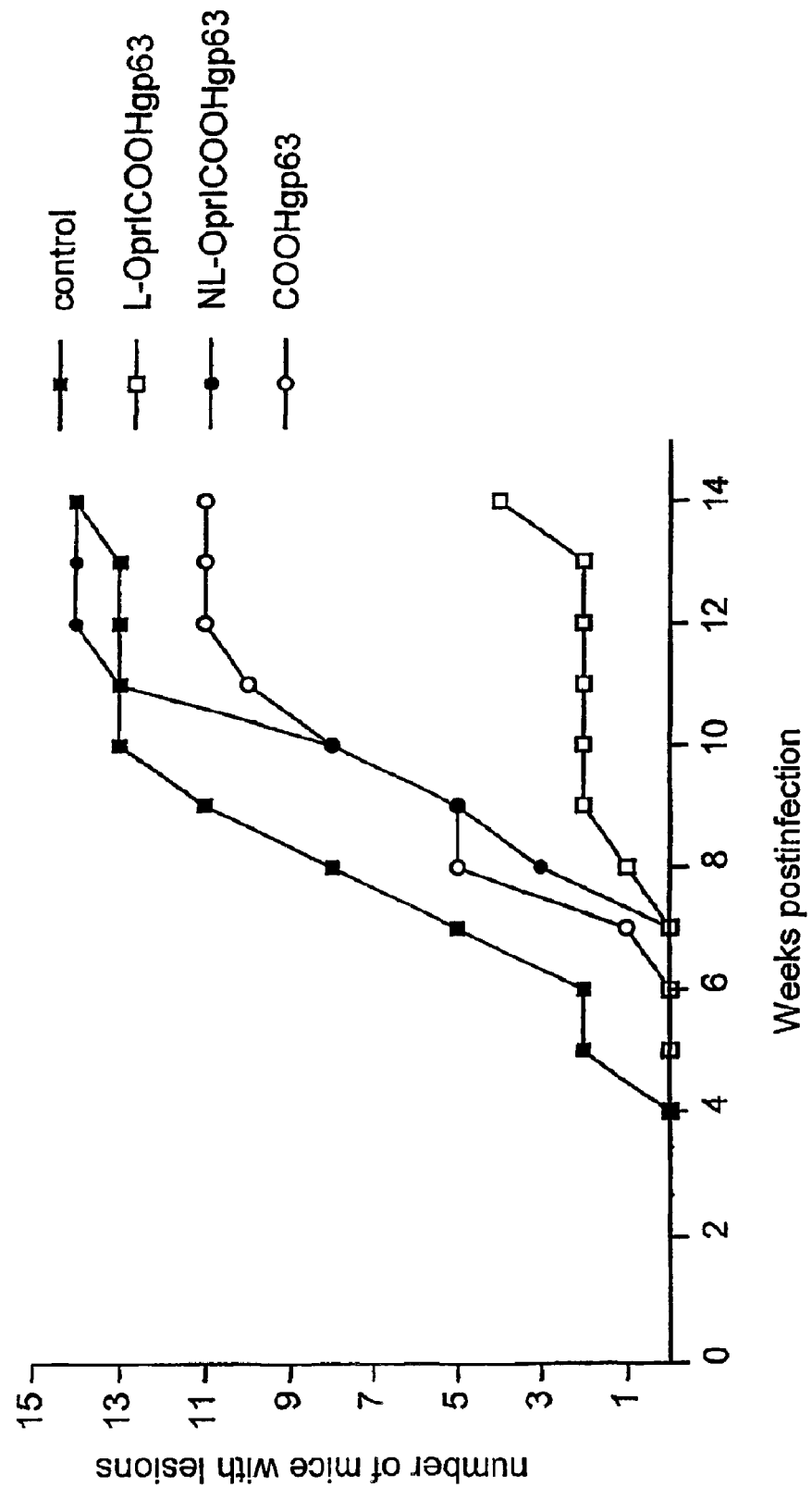
FIG. 8: The OprI-based COOHgp63 lipoprotein protects BALB/c mice against Leishmania challenge. Groups of 15 mice were vaccinated subcutaneously three times with the lipidated L-OprICOOHgp63, the non-lipidated NL-OprICOOHgp63 or COOHgp63. Controls were injected with buffer. Mice were infected with $10^6$ live promastigotes 10 days after the last immunization and lesion development was monitored weekly.

Vaccinations with OprI-Based COOHgp63 Lipoproteins Protect Highly Susceptible BALB/c Mice Against *Leishmania* Challenge It is well established that during infection with *L. major*, resistant C57BL/6 mice mount a polarized Type-1 cellular immune response mediated by IFN-$\gamma$ production (Reiner and Locksley, 1995; Milon et al., 1995). In view of the capacity of the lipid-modified OprICOOHgp63 to skew the immune response towards an IFN-$\gamma$-producing Type-1 immune response, it was of interest to test whether vaccinations with this lipoprotein could provide protection in highly susceptible BALB/c mice against *Leishmania* challenge. To this end, mice were vaccinated with the lipidated OprICOOHgp63, the non-lipidated counterpart or COOHgp63 in order to compare the effect of immunization on lesion development. As shown in FIG. 8, a clear delay in the onset of skin lesions in mice vaccinated with the lipid-modified protein was observed. In the groups vaccinated with the non-lipidated OprICOOHgp63 and the COOHgp63, the pattern of disease appearance was similar to the control group although a slight delay was observed. After 14 weeks of infection, 73% of L-OprICOOHgp63-vaccinated animals still remained healthy, indicating that vaccination with the lipid-modified protein delayed the appearance of the disease and induced a protective immunity in the majority of the animals.

It is well established that immunological control of *L. major* infections depends on the production of IFN-$\gamma$ that activates macrophages to kill the parasites via induction of NO production (Milon et al., 1995; Mossalayi et al., 1999; Green et al., 1990). Accordingly, the capacity of L-OprICOOHgp63 to elicit COOHgp63-specific IFN-$\gamma$-producing memory cells is reflected by the induction of protective immunity against *L. major* infections in the highly susceptible BALB/c model. Taking into account that this type of immunization is highly TNF-$\alpha$-dependent, it is worth mentioning that vaccination with leishmanial antigens together with TNF-$\alpha$ prevents disease enhancement and induces protective immunity against *L. major* infection in susceptible BALB/c mice (Liew et al., 1991).

Example IV

Induction of Type-1 Immune Responses Against a Heterologous Antigen by Immunization with a Host Cell Expressing an OprI-Heterologous Antigen Fusion Protein To see whether L-OprI pathogen-derived antigens/peptides, presented in the context of L-OprI at the surface of live host cells, can induce a relevant immune response, a live vaccination experiment was carried out using a L-OprI/FMDV antigen presented at the surface of attenuated *Salmonella typhimurium* SL3261 (Hoiseth & Stocker, 1981).

BALB/c mice (8 weeks of age) were immunized intranasally with $10^8$ *S. typhimurium* SL3261 (pVUB3:3D-15) in a 10 μl volume (5 μl per nostril). Three months after the intranasal immunization, mice were killed. Sera and spleens were taken to analyze the immune response.

Homogeneous spleen cell suspensions from individual mice were prepared in supplemented RPMI 1640 medium. $2\times10^6$ cells were restimulated with either 6×His-3D, NL-OprI, ovalbumin (irrelevant antigen) or crude *Salmonella* SL3261 lysate. The cytokine levels were determined in the culture supernatants taken 24, 48, 72 and 96 h after restimulation. Antibody isotypes against recombinant 6×His-3D protein, NL-OprI or crude *Salmonella* SL3261 lysate were determined in naive and immune sera by ELISA. Serum was applied to every separate antigen (2 μg/ml) and detected with specific anti-isotype antibodies. Total anti-3D IgG titers are in the range of 1/10000.

A single immunization with SL3261 (pVUB3:3D-15) biased the T-cell response against the heterologous 3D antigen towards IFN-γ production (FIGS. 10A and 10B), indicating a preferential induction of a Type-1 immune response. Besides the induction of IFN-γ producing cells, this immunization also elicited a selective humoral (IgG2a) Type-1 immune response against 3D (FIG. 11).

Example V

OprI-Derived Fusion Proteins Induce a Long-Lasting Type-1 Immune Response

BALB/c mice were s.c. immunized three times at 10-day intervals with 1 μg OprI-COOHgp63 antigen. Spleen cells and sera were taken at 2 and 12 weeks after the last immunization and analyzed for the production of cytokines and antibodies. The results are shown in FIGS. 12A and 12B, indicating that both antibody response and IFN-γ production is hardly affected by the time.

Example VI

OprI Retains its Type-1 Adjuvanticity When Admixed with a Heterologous Antigen as Demonstrated in the *Leishmania* Model BALB/c mice were s.c. immunized three times at 10-day intervals with 1 μg OprI-COOHgp63 antigen or L-OprI+6×His-COOHgp63 at a same molar basis as the covalent formulation. Spleen cells and sera were taken 2 weeks after the last immunization and analyzed for the production of cytokines and antibodies. The results are shown in FIGS. 13A and 13B. Although there are some differences in IgG3 response and IFN-γ production, it is clear that the response obtained by the OprI+COOHgp63 mixture is mainly a Type-1 response.

Example VII

L-OprI Incytes Cytolytic CD8 T-Cells Towards MHC-Class-1 Restricted T-Cell Epitopes in a Th Cell-Independent Way In view of the capacity of L-OprI to induce Type-1 humoral and cellular responses against a heterologous antigen fused to its C-terminal or admixed therewith, it was of interest to look for the possible adjuvant capacity of L-OprI to induce specific cytotoxic T lymphocytes against a heterologous antigen or peptide. To this end, we evaluated the CTL-inducing capacity of L-OprI in an OVA-model when admixed with free protein or peptides as compared to other adjuvants.

C57BL/6 mice were immunized with i) 1 μg OprI+5 μg OVA$_{257-264}$ MHC class I (K$^b$-restricted) peptide, ii) 1 μg OprI+5 μg OVA$_{257-264}$ MHC class I (K$^b$-restricted) peptide+5 μg OVA$_{265-280}$ MHC class II (I-Ab-restricted) T$_h$ peptide, iii) PBS+5 μg OVA$_{257-264}$ MHC class I (K$^b$-restricted) peptide, iv) CFA+5 μg OVA$_{257-264}$ MHC class I (K$^b$-restricted) peptide, v) 1 μg L-OprI+1 μg OVA protein, and vi) 1 μg OVA in PBS.

Mice were immunized three times subcutaneously (s.c.) at the base of the tail, at 10-day intervals. The CTL assay was set up 10 days after the last immunization. Each mouse was analyzed individually; each group consisted of 4 mice.

Figure 14:
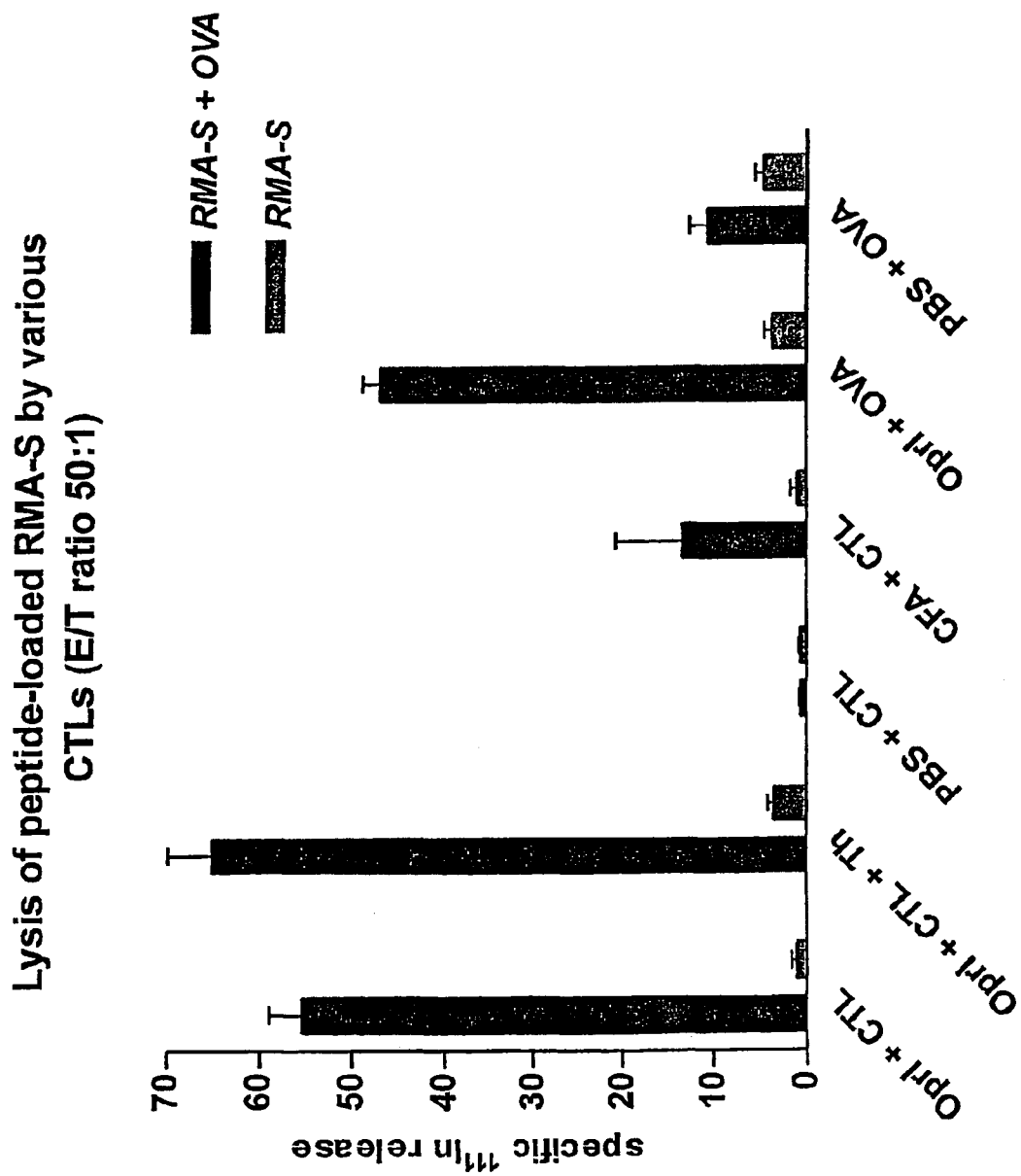
FIG. 14: Lysis of OVA$_{257-264}$ peptide-loaded RMA-S cells by cytotoxic T-cell lymphocytes (CTLs), induced against the OVA$_{257-264}$ (SIINFEKL) epitope, in the presence of various adjuvants. OprI+CTL is 1 µg OprI and 5 µg OVA$_{257-264}$ MHC class I ($K^b$-restricted) peptide. OprI+CTL+Th is 1 µg OprI, 5 µg OVA$_{257-264}$ MHC class I ($K^b$-restricted) peptide and 5 µg OVA$_{265-280}$ (MHC class II (I-Ab-restricted) $T_h$ peptide. PBS+CTL is PBS and 5 µg OVA$_{257-264}$ MHC class I ($K^b$-restricted) peptide. CFA+CTL is CFA and 5 µg OVA$_{257-264}$ MHC class I ($K^b$-restricted) peptide. OprI+OVA is 1 µg L-OprI and 1 µg OVA protein. PBS+OVA is 1 µg OVA in PBS. RMA-S+OVA is RMA-S cells loaded with OVA$_{257-264}$ peptide. RMA-S is non-loaded RMA-S cells.

As shown in FIG. 14, splenocytes from all groups of mice immunized with OprI+antigen/peptide lysed significantly more OVA$_{257-264}$ peptide-loaded RMA-S target cells as compared to the unloaded RMA-S target cells. Immunization with antigen/peptide in PBS did not induce a specific cytolytic activity. As compared to CFA, OprI seems to be a more potent adjuvant for the induction of CTLs against a minimal CTL epitope.

In conclusion, L-OprI was shown to incite cytolytic CD8 T-cells toward MHC class I-restricted T-cell epitopes in a Th cell-independent manner, which could be further potentiated by the addition of T-helper epitope.

Example VIII

Figure 16:
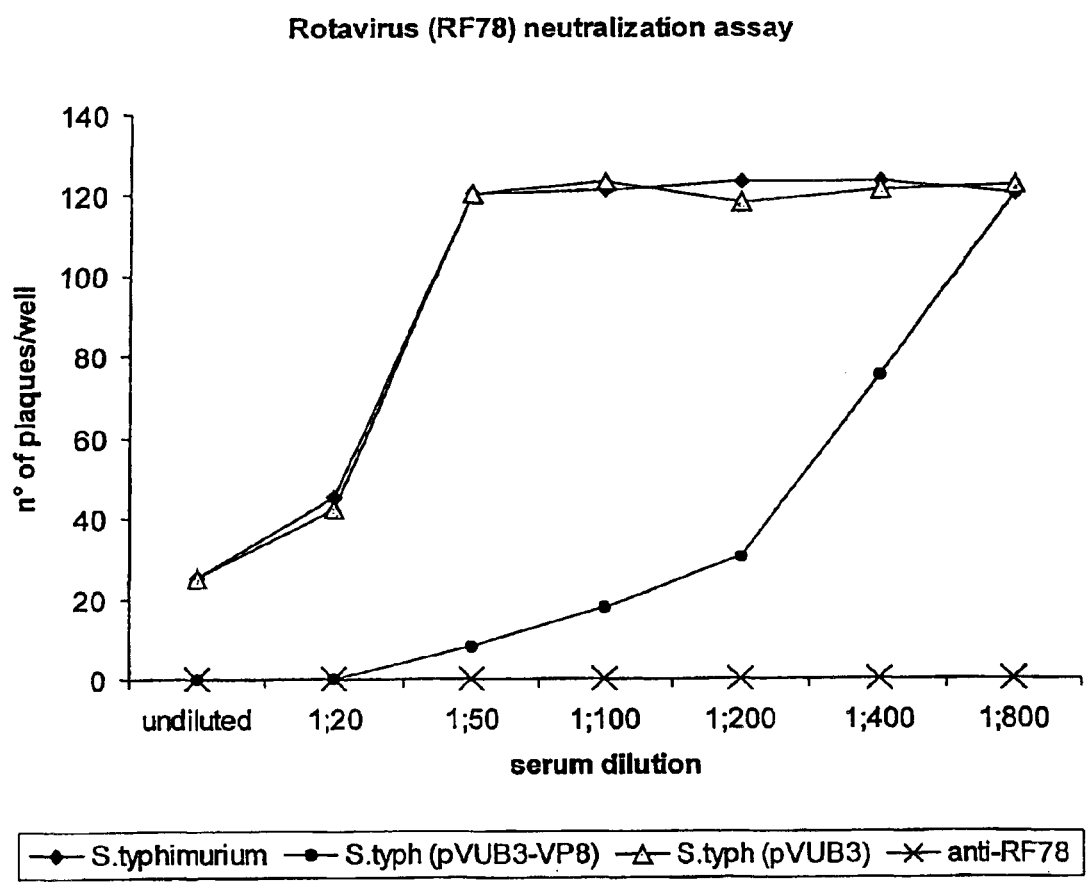
FIG. 16: Rotavirus strain RF78 neutralization assay using sera collected from mice immunized with *Salmonella typhimurium* $\chi$4046 (*S. typhimurium*), *S. typhimurium* $\chi$4046 transformed with pVUB3 (*S. typh* (pVUB3)) and *S. typhimurium* $\chi$4046 transformed with pVUB3-VP8 (*S. typh* (pVUB3-VP8)). Anti-RF78 represents the positive control using polyclonal anti-RF78 antibodies (obtained from Dr. Cohen, INRA, France).

Live Oral Vaccination with Recombinant *Salmonella* Expressing an OprI-Rotavirus Recombinant Antigen Elicits Specific Neutralizing Antibodies Against Rotavirus To see whether live oral vaccination using L-OprI as a carrier for the presentation of heterologous antigens on the surface of a host cell can induce the appropriate immune response, immunization experiments were performed with *S. typhimurium* $_\chi$4064 (Curtiss & Kelly, 1987) harboring pVUB3:VP8 rotavirus antigen. BALB/c mice were immunized once intranasally with recombinant *S. typhimurium* (strain $_\chi$4064) expressing i) L-OprI-rotavirus (VP8) recombinant antigen, ii) L-OprI or iii) *S. typhimurium* $_\chi$4064 alone. Subsequent analysis of the serum taken from all groups of mice revealed the presence of VP8-specific antibodies in the group immunized with *S. typhimurium* $_\chi$4064 expressing L-OprI-rotavirus (VP8) recombinant antigen. To see whether the elicited VP8-specific antibodies could neutralize rotavirus strain RF78 (kindly provided by Dr. Cohen, INRA, France), 100 pfu of rotavirus strain RF78 was mixed with different dilutions of sera collected from mice immunized with either *S. typhimurium* $_\chi$4064, $_\chi$4064(pVUB3), or $_\chi$4064(pVUB3-VP8), and tested for plaque reduction. Polyclonal antibodies against RF78 (a polyclonal serum against rotavirus strain RF78 was prepared and provided by Dr. Cohen, INRA, France) were used as a positive control. As can be seen from FIG. 16, serum from $_\chi$4064(pVUB3-VP8)-immunized mice could partially neutralize the rotavirus. The titer of neutralization was determined as 60% of plaque reduction.

REFERENCES

Aliprantis, A. O., Yang R. B., Mark, M. R., Suggett, S., Devaux, B., Radolf, J. D., Klimpel, G. R., Godowski, P. & Zychlinsky, A. Cell activation and apoptosis by bacterial lipoproteins through toll-like receptor-2. *Science* 285, 736–739 (1999).

BenMohamed, L. Gras-Masse, H., Tartar, A., Daubersies, P., Brahimi, K., Bossus, M., Thomas, A. & Druilhe P. Lipopeptide immunization without adjuvant induces potent and long-lasting B, T helper, and cytotoxic T lymphocyte responses against a malaria liver stage antigen in mice and chimpanzees. *Eur. J Immunol.* 27, 1242–1253 (1997).

Bessler, W. G., Suhr, B., Buhring, H. J., Muller, C. P., Wiesmuller, K. H., Becker, G. & Jung, G. Specific antibodies elicited by antigen covalently linked to a synthetic adjuvant. *Immunobiology* 170, 239–244 (1985).

Brightbill, H. D., Libraty, D. H., Krutzik, S. R., Yang, R. B., Belisle, J. T., Bleharski, J. R., Maitland, M., Norgard, M. V., Plevy, S. E., Smale, S. T., Brennan, P. J., Bloom, B. R., Godowski, P. J. & Modlin, R. L. Host defense mechanisms triggered by microbial lipoproteins through toll-like receptors. *Science* 285, 732–736, (1999).

Butler, D. M., Malfait, A. M., Maini, R. N., Brennan, F. M. & Feldmann, M. Anti-IL-12 and anti-TNF antibodies synergistically suppress the progression of murine collagen-induced arthritis. *Eur. J. Immunol.* 29, 2205–2212 (1999).

Cornelis, P. Sierra, J. C., Lim, A., Malur, A., Tungpradabkul, S., Tazka, H., Leitao, A., Martins, C. V., di Pema, C., Brys, L., De Baetseller, P. & Hamers, R. Development of new cloning vectors for the production of immunogenic outer membrane fusion proteins in *Escherichia coli*. *Biotechnology* (N.Y.) 14, 203–208 (1996).

Cote-Sierra, J., Jongert, E., Bredan, A., Gautam, D. C., Parkhouse, M., Cornelis, P., DeBaetselier, P. & Revets, H. A new membrane-bound OprI lipoprotein expression vector. High production of heterologous fusion proteins in gram (-) bacteria and the implications for oral vaccination. *Gene* 221, 25–34 (1998).

Curtiss, R. & Kelly, S. M. *Salmonella typhimurium* deletion mutants lacking adenylate cyclase and cyclic AMP receptor protein are avirulent and immunogenic. *Infect. Immun.* 55, 3035–3043 (1987).

Daiji, A., Beschin, A., Sileghem, M., Heremans, H., Brys, L. & De Baetselier, P. In vitro 5 simulation of immunosuppression caused by *Typanosoma brucei*: active involvement of gamma interferon and tumor necrosis factor in the pathway of suppression. *Infect. Immun.* 64, 1937–1943 (1996).

Deres, K., Schild, H., Wiesmuller, K. H., Jung, C. & Rammensee, H. G. In vivo priming of virus-specific cytotoxic T lymphocytes with synthetic lipopeptide vaccine. *Nature* 342, 561–564 (1989).

de Jong, R., Janson, A. A., Faber, W. R., Naafs, B. & Ottenhoff, T. H. IL-2 and IL-12 act in synergy to overcome antigen-specific T-cell unresponsiveness in mycobacterial disease. *J. Immunol.* 159, 786–793 (1997).

Donckier, V., Abramowicz, D., Bruyns, C., Florquin, S., Vanderhaeghen, M. L., 15 Amraoui, Z., Dubois, C., Vandenabeele, P. and Goldman, M. IFN-gamma prevents Th2 cell-mediated pathology after neonatal injection of semiallogenic spleen cells in mice. *J. Immunol.* 153, 2361–2368 (1994).

Erdile, L. F., Brandt, M. A., Warakomski, D. J., Westrack, G. J., Sadziene, A., Barbour, A. G. & Mays, J. P. Role of attached lipid in immunogenicity of *Borrelia burgdorferi* OspA. *Infect. Immun.* 61, 81–90 (1993).

Fearon, D. T. & Locksley, R. M. The instructive role of innate immunity in the acquired immune response. *Science* 272, 50–53 (1996).

Green, S. J., Crawford, R. M., Hockmeyer, J. T., Meltzer, M. S. & Nacy, C. A. *Leishmania major* amastigotes initiate the L-arginine-dependent killing mechanism in IFN-γ-stimulated macrophages by induction of tumor necrosis factor-alpha. *J. Immunol.* 145, 4290–4297(1990).

Heinzel, F. P., Sadick, M. D., Mutha, S. S. & Locksley, R. M. Production of IFN-γ, IL-2, IL-4 and IL-10 by CD4$^+$ lymphocytes in vivo during healing and progressive murine leishmaniasis. *Proc. Natl. Acad. Sci. USA* 88, 7011–7015 (1991).

Hoekstra, D., van der Laan, J. W., de Leij, L. & Witholt, B. Release of outer membrane fragments from normally growing *Escherichia coli*. *Biochim. Biophys. Acta* 455, 889–899 (1976).

Hoiseth, S. K. & Stocker B. A. D. Aromatic-dependent *Salmonella typhimurium* are non-virulent and effective as live vaccines. *Nature* 291, 238–240 (1981).

Infante-Duarte, C. & Kamradt, T. Lipopeptides of *Borrelia burgdorferi* outer surface 10 proteins induce Th1 phenotype development in αβ T-cell receptor transgenic mice. *Infect. Immun.* 65, 4094–4099 (1997).

Ino, M., Nagase, S., Nagasawa, T. Koyama, A. & Tachibana, S. The outer membrane protein I of *Pseudomonas aeruginosa* PA01, a possible pollutant of dialysate in hemodialysis, induces cytokines in mouse bone marrow cells. *Nephron*, 82, 324–330 (1999).

Kupiec-Weglinski, J. W., Austyn, J. M. & Morris, P. J. Migration patterns of dendritic cells in the mouse. Traffic from blood, and T-cell-dependent and -independent entry to lymphoid tissues. *J. Exp. Med.* 167, 632–645 (1988).

Leitao, A., Malur, A., Cornelis, P. & Martins, C. L. Identification of a 25-amino acid sequence from the major African swine fever virus structural protein VP72 recognized by porcine cytotoxic T lymphocytes using a lipoprotein based expression system. *J. Virol. Methods* 75, 113–119 (1998).

Leonard, J. P., Waldburger, K. E. & Goldman, S. J. Prevention of experimental autoimmune encephalomyelitis by antibodies against interleukin 12. *J. Exp. Med.* 181, 381–386 (1995).

Lex, A., Wiesmuller, K. H., Jung, C. & Bessler, W. G. A synthetic analogue of *Escherichia coli* lipoprotein, tripalmitoyl pentapeptide, constitutes a potent immune adjuvant. *J. Immunol.* 137, 2676–2681 (1986).

Liew, F. W., Li, Y., Yang, D. M., Severn, A. & Cox, F. E. TNF-α reverses the disease-exacerbating effect of subcutaneous immunization against murine cutaneous leishmaniasis. *Immunology* 74, 304–309 (1991).

Milon, C., Del Giudice, C. & Louis, J. A. Immunobiology of Experimental Cutaneous Leishmaniasis. *Parasitol. Today* 11, 244–247 (1995).

Mosmann, T. R. & Coffman, R. C. Th1 and Th2 cells: different patterns of lymphokine secretion lead to different functional properties. *Annu. Rev. Immunol.*, 7, 145– (1989).

Mossalayi, M. D., Arock, M., Mazier, D., Vincendeau, P. & Vouldoukis, I. The human immune response during cutaneous leishmaniasis: NO problem. *Parasitol. Today* 15, 342–345 (1999).

Murphy, J. W., Wu-Hsieh, B. A., Singer-Vermes, L. M. Ferrante, A., Moser, S., Ruso, M., Vaz, S. A., Burger, E., Calich, V. L. & Kowanko, I. C. Cytokines in the host response to mycotic agents. *J. Med. Vet. Mycol.* 32 Suppl 1, 203 (1994).

Nabors, G. S., Afonso, L. C. C., Farrell, J. PO. & Scott, P. Switch from a type 2 to a type 1 T helper cell response and cure of established *Leishmania major* infection in mice is induced by combination therapy with interleukin 12 and pentosam. *Proc. Natl. Acad. Sci. USA*, 92, 3142–3146 (1995).

Pasparakis, M., Alexopoulou, L., Episkopou, V. & Kollias, G. Immune and inflammatory responses in TNF alpha-deficient mice: a critical requirement for TNF alpha in the formation of primary B cell follicles, follicular dendritic cell networks and germinal centers, and in the maturation of the humoral immune response [see comments]. *J. Exp. Med.* 184,1397–1411 (1996).

Racke, M. K., Bonomo, A., Scott, D. E., Canella, B., Levine, A., Raine, C. S., Shevach, E. M. & Rocken, M. Cytokine induced immune deviation as a therapy for inflammatory autoimmune disease. *J. Exp. Med.*, 180, 1961–1966 (1994).

Racke, M. K., Burnett, D., Pak, S. H., Albert, P. S., Cannella, B., Raine, C. S., McFarlin, D. E. & Scott, D. E. Retinoid treatment of experimental allergic encephalomyelitis. IL-4 production correlates with improved disease course. *J. Immunol.*, 154, 450–458 (1995).

Radolf, J. D., Norgard, M. V., Brandt, M. E., Isaacs, R. D., Thompson, P. A. & Beutler, B. Lipoproteins of *Borrelia burgdorferi* and *Treponema pallidum* activate cachectin/tumor necrosis factor synthesis. Analysis using a CAT reporter construct. *J. Immunol* 147, 1968–1974 (1991).

Reiner, S. L. & Locksley, R. M. The regulation of immunity to *Leishmania major. Annu. Rev. Immunol.* 13, 151–177 (1995).

Swallow, M. M., Waflin, J. J. & Sha, W.C. B7h, a novel costimulatory homolog of B7.1 and B7.2, is induced by TNFalpha. *Immunity*, 11, 423–432 (1999).

Taniguchi, T., Takata, M., Ikeda, A., Momotani, E. & Sekikawa, K. Failure of germinal center formation and impairment of response to endotoxin in tumor necrosis factor alpha-deficient mice. *Lab Invest.* 77, 647–658 (1997).

Tripp, C. S., Wolf, S. F. & Unanue, E. R. Interleukin 12 and tumor necrosis factor a are costimulators of interferon y production by natural killer cells in severe combined immunodeficiency mice with listeriosis, and interleukin 10 is a physiologic antagonist. *Proc. Natl. Acad. Sci. USA*. 90, 3725–3729 (1993).

Vidal, V., Scragg, I. G., Cutler, S. J., Rockett, K. A., Fekade, D., Warrefl, D. A., Wright, D. J. & Kwiatkowski, D. Variable major lipoprotein is a principal TNF-inducing factor of louse-borne relapsing fever. *Nat. Med.* 4, 1416–1420 (1998).

Vogel, G. New clues to asthma therapies. *Science*, 276, 1643–1646 (1997).

Weis, J. J., Ma, Y. & Erdile, L. F. Biological activities of native and recombinant *Borrelia burgdorferi* outer surface protein A: dependence on lipid modification. *Infect. Immun.* 62, 4632–4636 (1994).

Yamamura, M., Uyemura, K. and Deans, R. J. Defining protective responses to pathogens: cytokine profiles in leprosy lesions. *Science*, 254, 277–279 (1991).

Yang, D. M., Rogers, M. V. & Liew, F. W. Identification and characterization of host-protective T-cell epitopes of a major surface glycoprotein (Gp63) from *Leishmania major Immunology*. 72, 3–9 (1991).

What is claimed is:

1. A method of producing a Th1 immune response in a subject, said method comprising:

administering to a subject, at least a lipidated tail of an outer membrane lipoprotein OprI comprising SEQ ID NO: 1 fused to a heterologous antigen, wherein the outer membrane lipoprotein OprI has the function of eliciting a Th1 immune response, as an adjuvant to a heterologous antigen, thereby obtaining a Th1 immune response against the heterologous antigen.

2. The method according to claim 1, wherein the heterologous antigen is gp63 of *Leishmania major*.

3. The method according to claim 1 wherein the subject's natural Th1 immune response to a disease is insufficient to suppress a Th2 immune response or in which the immune response is polarized towards a Th2 immune response.

4. The method according to claim 2 wherein the subject's natural Th1 immune response to a disease is insufficient to suppress a Th2 immune response or in which the immune response is polarized towards a Th2 immune response.

5. The method according to claim 3 wherein the disease is selected from the group consisting of *Leishmaniasis*, tuberculosis (TBC), leprosy, mycotic infection, autoimmune disease, and allergic asthma.

6. The method according to claim 4 wherein the disease is selected from the group consisting of *Leishmaniasis*, tuberculosis (TBC), leprosy, mycotic infection, autoimmune disease, and allergic asthma.

7. A method of producing a Th1 immune response in a subject, said method comprising:

administering to a subject, at least a lipidated tail of an outer membrane lipoprotein OprI, as a adjuvant; and administering a heterologous antigen, wherein the heterologous antigen is not covalently bound to the adjuvant, thereby increasing production of a Th1 immune response against the heterologous antigen in the subject.

8. The method according to claim 7, wherein the heterologous antigen comprises an immunogenic fragment of gp63 of *Leishmania major*.

9. The method according to claim 7, wherein the subject's natural Th1 immune response to a disease is insufficient to suppress a Th2 immune response or in which the immune response is polarized towards a Th2 immune response.

10. The method according to claim 7, wherein the disease is selected from the group consisting of *Leishmaniasis*, tuberculosis (TBC), leprosy, mycotic infection, autoimmune disease, and allergic asthma.

* * * * *

SEQUENCE LISTING

<160> NUMBER OF SEQ ID NOS: 6

<210> SEQ ID NO 1
<211> LENGTH: 54

-continued

<212> TYPE: PRT
<213> ORGANISM: Pseudomonas aeruginosa

<400> SEQUENCE: 1

Cys Ser Ser His Ser Lys Glu Thr Glu Ala Arg Leu Thr Ala Thr Glu
1               5                   10                  15

Asp Ala Ala Arg Ala Gln Ala Arg Ala Asp Glu Ala Tyr Arg Lys
            20                  25                  30

Ala Asp Glu Ala Leu Gly Lys Ala Gly Gly Thr Ala Asp Glu Ala Asn
        35                  40                  45

Glu Arg Ala Leu Arg Met
        50

<210> SEQ ID NO 2
<211> LENGTH: 1884
<212> TYPE: DNA
<213> ORGANISM: Artificial Sequence
<220> FEATURE:
<223> OTHER INFORMATION: OprI-3D-FMDV15 fusion
<220> FEATURE:
<221> NAME/KEY: CDS
<222> LOCATION: (1)..(1884)
<223> OTHER INFORMATION: OprI-3D-FMDV15 fusion.

<400> SEQUENCE: 2

```
atg aac aac gtt ctg aaa ttc tct gct ctg gct ctg gct gct gtt ctg      48
Met Asn Asn Val Leu Lys Phe Ser Ala Leu Ala Leu Ala Ala Val Leu
1               5                   10                  15 gcc acc ggt tgc agc agc cac tcc aaa gaa acc gaa gct cgt ctg acc      96
Ala Thr Gly Cys Ser Ser His Ser Lys Glu Thr Glu Ala Arg Leu Thr
            20                  25                  30 gct acc gaa gac gca gct gct cgt gct cag gct cgc gct gac gaa gcc     144
Ala Thr Glu Asp Ala Ala Ala Arg Ala Gln Ala Arg Ala Asp Glu Ala
        35                  40                  45 tat cgc aag gct gac gaa gct ctg ggc gct gct cag aaa gct cag cag     192
Tyr Arg Lys Ala Asp Glu Ala Leu Gly Ala Ala Gln Lys Ala Gln Gln
    50                  55                  60 acc gct gac gag gct aac gag cgt gcc ctg cgc atg cag atc atc ggg     240
Thr Ala Asp Glu Ala Asn Glu Arg Ala Leu Arg Met Gln Ile Ile Gly
65                  70                  75                  80 ttg att gtg gac acc aga gat gtg gaa gag cgc gtt cac gtg atg cgc     288
Leu Ile Val Asp Thr Arg Asp Val Glu Glu Arg Val His Val Met Arg
                85                  90                  95 aaa acc aag ctt gca ccc acc gtt gca cac ggt gtg ttc aac ccc gag     336
Lys Thr Lys Leu Ala Pro Thr Val Ala His Gly Val Phe Asn Pro Glu
            100                 105                 110 ttt ggg ccc gct gcc ttg tcc aac aag gac ccg cgt ctg aac gag ggt     384
Phe Gly Pro Ala Ala Leu Ser Asn Lys Asp Pro Arg Leu Asn Glu Gly
        115                 120                 125 gtt gtc ctc gac gaa gtc atc ttc tcc aaa cac aag gga gac aca aag     432
Val Val Leu Asp Glu Val Ile Phe Ser Lys His Lys Gly Asp Thr Lys
    130                 135                 140 atg tct gag gag gac aaa gcg ctg ttc cgc cgc tgc gct gct gac tac     480
Met Ser Glu Glu Asp Lys Ala Leu Phe Arg Arg Cys Ala Ala Asp Tyr
145                 150                 155                 160 gcg tca cgc ttg cac agc gtg ttg ggc aca gca aat gcc cca ctg agc     528
Ala Ser Arg Leu His Ser Val Leu Gly Thr Ala Asn Ala Pro Leu Ser
                165                 170                 175 atc tac gag gca atc aag ggt gtc gac gga ctc gac gcc atg gaa cca     576
Ile Tyr Glu Ala Ile Lys Gly Val Asp Gly Leu Asp Ala Met Glu Pro
            180                 185                 190
```

```
gac act gcg ccc ggc ctc ccc tgg gcc ctc cag ggt aaa cgc cgc ggc     624
Asp Thr Ala Pro Gly Leu Pro Trp Ala Leu Gln Gly Lys Arg Arg Gly
            195                 200                 205 gcg ctc atc gac ttc gag aac ggc acg gtc gga ccc gaa gtt gag gct     672
Ala Leu Ile Asp Phe Glu Asn Gly Thr Val Gly Pro Glu Val Glu Ala
    210                 215                 220 gcc ctg aag ctc atg gag aag aga gaa tac aaa ttt gtt tgt cag acc     720
Ala Leu Lys Leu Met Glu Lys Arg Glu Tyr Lys Phe Val Cys Gln Thr
225                 230                 235                 240 ttc ctg aag gac gag att cgc ccg ttg gag aaa gta cgt gcc ggt aag     768
Phe Leu Lys Asp Glu Ile Arg Pro Leu Glu Lys Val Arg Ala Gly Lys
                245                 250                 255 act cgc att gtc gac gtc ctg ccc gtt gag cac att ctt tac acc agg     816
Thr Arg Ile Val Asp Val Leu Pro Val Glu His Ile Leu Tyr Thr Arg
        260                 265                 270 atg atg att ggc aga ttt tgt gca cag atg cac tca aat aac gga ccg     864
Met Met Ile Gly Arg Phe Cys Ala Gln Met His Ser Asn Asn Gly Pro
    275                 280                 285 caa att ggc tca gcg gtc ggt tgc aac cct gat gtt gat tgg cag aga     912
Gln Ile Gly Ser Ala Val Gly Cys Asn Pro Asp Val Asp Trp Gln Arg
290                 295                 300 ttt ggc aca cac ttc gcc cag tac aga aac gtg tgg gat gtg gac tat     960
Phe Gly Thr His Phe Ala Gln Tyr Arg Asn Val Trp Asp Val Asp Tyr
305                 310                 315                 320 tcg gcc ttt gat gct aat cac tgt agt gat gcc atg aac atc atg ttt    1008
Ser Ala Phe Asp Ala Asn His Cys Ser Asp Ala Met Asn Ile Met Phe
                325                 330                 335 gag gag gtg ttt cgc acg gag ttc ggc ttc cac ccg aat gct gag tgg    1056
Glu Glu Val Phe Arg Thr Glu Phe Gly Phe His Pro Asn Ala Glu Trp
        340                 345                 350 atc ctg aag act ctt gtg aac acg gaa cac gcc tat gag aac aaa cgc    1104
Ile Leu Lys Thr Leu Val Asn Thr Glu His Ala Tyr Glu Asn Lys Arg
    355                 360                 365 atc act gtt gga ggc gga atg ccg tct ggt tgc tcc gca aca agc atc    1152
Ile Thr Val Gly Gly Gly Met Pro Ser Gly Cys Ser Ala Thr Ser Ile
370                 375                 380 atc aac aca att ttg aac aac atc tac gtg ctc tac gcc ctg cgt aga    1200
Ile Asn Thr Ile Leu Asn Asn Ile Tyr Val Leu Tyr Ala Leu Arg Arg
385                 390                 395                 400 cac tat gag gga gtt gag ctg gac aca tac acc atg atc tcc tac gga    1248
His Tyr Glu Gly Val Glu Leu Asp Thr Tyr Thr Met Ile Ser Tyr Gly
                405                 410                 415 gac gac atc gtg gtg gca agt gat tat gat ttg gac ttc gag gct ctc    1296
Asp Asp Ile Val Val Ala Ser Asp Tyr Asp Leu Asp Phe Glu Ala Leu
        420                 425                 430 aag ccc cac ttt aaa tcc ctt ggc caa acc atc act cca gct gac aaa    1344
Lys Pro His Phe Lys Ser Leu Gly Gln Thr Ile Thr Pro Ala Asp Lys
    435                 440                 445 agc gac aaa ggt ttt gtt ctt ggt cac tcc att acc gat gtc act ttc    1392
Ser Asp Lys Gly Phe Val Leu Gly His Ser Ile Thr Asp Val Thr Phe
450                 455                 460 ctc aaa agg cac ttc cac atg gac tat gga act ggg ttt tac aaa cct    1440
Leu Lys Arg His Phe His Met Asp Tyr Gly Thr Gly Phe Tyr Lys Pro
465                 470                 475                 480 gtg atg gcc tca aag acc ctt gag gct atc ctc tcc ttt gca cgc cgt    1488
Val Met Ala Ser Lys Thr Leu Glu Ala Ile Leu Ser Phe Ala Arg Arg
                485                 490                 495 ggg acc ata cag gag aag ttg atc tcc gtg gca gga ctc gcc gtc cac    1536
Gly Thr Ile Gln Glu Lys Leu Ile Ser Val Ala Gly Leu Ala Val His
        500                 505                 510
```

```
tct gga cca gac gag tac cgg cgt ctc ttt gag cct ttc caa ggt ctc   1584
Ser Gly Pro Asp Glu Tyr Arg Arg Leu Phe Glu Pro Phe Gln Gly Leu
        515                 520                 525 ttt gag att cca agc tac aga tca ctt tac ctg cgt tgg gtg aac gcc   1632
Phe Glu Ile Pro Ser Tyr Arg Ser Leu Tyr Leu Arg Trp Val Asn Ala
530                 535                 540 gtg tgc ggt gac gcg ctg gtt ccg cgt gga tcc tgc cgg cac aaa caa   1680
Val Cys Gly Asp Ala Leu Val Pro Arg Gly Ser Cys Arg His Lys Gln
545                 550                 555                 560 aaa ata gtg gcg cca gta aaa caa aca cta cca cca tca aac cta cga   1728
Lys Ile Val Ala Pro Val Lys Gln Thr Leu Pro Pro Ser Asn Leu Arg
                565                 570                 575 gga gat cta caa gta cta gca caa aaa gtg gcg cgc aca cta cca tgc   1776
Gly Asp Leu Gln Val Leu Ala Gln Lys Val Ala Arg Thr Leu Pro Cys
            580                 585                 590 ggg aat tct gtt aac cgc atg ctg gaa aaa gcc agc cgc aag cat ggc   1824
Gly Asn Ser Val Asn Arg Met Leu Glu Lys Ala Ser Arg Lys His Gly
        595                 600                 605 tgc agc caa gct tgg ctg ttt tgg cgg atg aga gaa gat ttt cag ctt   1872
Cys Ser Gln Ala Trp Leu Phe Trp Arg Met Arg Glu Asp Phe Gln Leu
610                 615                 620 gat aca gat taa                                                   1884
Asp Thr Asp
625

<210> SEQ ID NO 3
<211> LENGTH: 627
<212> TYPE: PRT
<213> ORGANISM: Artificial Sequence
<220> FEATURE:
<223> OTHER INFORMATION: OprI-3D-FMDV15 fusion

<400> SEQUENCE: 3

Met Asn Asn Val Leu Lys Phe Ser Ala Leu Ala Leu Ala Ala Val Leu
1               5                   10                  15

Ala Thr Gly Cys Ser Ser His Ser Lys Glu Thr Glu Ala Arg Leu Thr
            20                  25                  30

Ala Thr Glu Asp Ala Ala Ala Arg Ala Gln Ala Arg Ala Asp Glu Ala
        35                  40                  45

Tyr Arg Lys Ala Asp Glu Ala Leu Gly Ala Ala Gln Lys Ala Gln Gln
    50                  55                  60

Thr Ala Asp Glu Ala Asn Glu Arg Ala Leu Arg Met Gln Ile Ile Gly
65                  70                  75                  80

Leu Ile Val Asp Thr Arg Asp Val Glu Glu Arg Val His Val Met Arg
                85                  90                  95

Lys Thr Lys Leu Ala Pro Thr Val Ala His Gly Val Phe Asn Pro Glu
            100                 105                 110

Phe Gly Pro Ala Ala Leu Ser Asn Lys Asp Pro Arg Leu Asn Glu Gly
        115                 120                 125

Val Val Leu Asp Glu Val Ile Phe Ser Lys His Lys Gly Asp Thr Lys
    130                 135                 140

Met Ser Glu Glu Asp Lys Ala Leu Phe Arg Arg Cys Ala Ala Asp Tyr
145                 150                 155                 160

Ala Ser Arg Leu His Ser Val Leu Gly Thr Ala Asn Ala Pro Leu Ser
                165                 170                 175

Ile Tyr Glu Ala Ile Lys Gly Val Asp Gly Leu Asp Ala Met Glu Pro
            180                 185                 190
```

-continued

```
Asp Thr Ala Pro Gly Leu Pro Trp Ala Leu Gln Gly Lys Arg Arg Gly
        195                 200                 205

Ala Leu Ile Asp Phe Glu Asn Gly Thr Val Gly Pro Glu Val Glu Ala
        210                 215                 220

Ala Leu Lys Leu Met Glu Lys Arg Glu Tyr Lys Phe Val Cys Gln Thr
225                 230                 235                 240

Phe Leu Lys Asp Glu Ile Arg Pro Leu Glu Lys Val Arg Ala Gly Lys
                245                 250                 255

Thr Arg Ile Val Asp Val Leu Pro Val Glu His Ile Leu Tyr Thr Arg
                260                 265                 270

Met Met Ile Gly Arg Phe Cys Ala Gln Met His Ser Asn Asn Gly Pro
            275                 280                 285

Gln Ile Gly Ser Ala Val Gly Cys Asn Pro Asp Val Asp Trp Gln Arg
        290                 295                 300

Phe Gly Thr His Phe Ala Gln Tyr Arg Asn Val Trp Asp Val Asp Tyr
305                 310                 315                 320

Ser Ala Phe Asp Ala Asn His Cys Ser Asp Ala Met Asn Ile Met Phe
                325                 330                 335

Glu Glu Val Phe Arg Thr Glu Phe Gly Phe His Pro Asn Ala Glu Trp
            340                 345                 350

Ile Leu Lys Thr Leu Val Asn Thr Glu His Ala Tyr Glu Asn Lys Arg
        355                 360                 365

Ile Thr Val Gly Gly Gly Met Pro Ser Gly Cys Ser Ala Thr Ser Ile
    370                 375                 380

Ile Asn Thr Ile Leu Asn Asn Ile Tyr Val Leu Tyr Ala Leu Arg Arg
385                 390                 395                 400

His Tyr Glu Gly Val Glu Leu Asp Thr Tyr Thr Met Ile Ser Tyr Gly
                405                 410                 415

Asp Asp Ile Val Val Ala Ser Asp Tyr Asp Leu Asp Phe Glu Ala Leu
            420                 425                 430

Lys Pro His Phe Lys Ser Leu Gly Gln Thr Ile Thr Pro Ala Asp Lys
        435                 440                 445

Ser Asp Lys Gly Phe Val Leu Gly His Ser Ile Thr Asp Val Thr Phe
    450                 455                 460

Leu Lys Arg His Phe His Met Asp Tyr Gly Thr Gly Phe Tyr Lys Pro
465                 470                 475                 480

Val Met Ala Ser Lys Thr Leu Glu Ala Ile Leu Ser Phe Ala Arg Arg
                485                 490                 495

Gly Thr Ile Gln Glu Lys Leu Ile Ser Val Ala Gly Leu Ala Val His
            500                 505                 510

Ser Gly Pro Asp Glu Tyr Arg Arg Leu Phe Glu Pro Phe Gln Gly Leu
        515                 520                 525

Phe Glu Ile Pro Ser Tyr Arg Ser Leu Tyr Leu Arg Trp Val Asn Ala
    530                 535                 540

Val Cys Gly Asp Ala Leu Val Pro Arg Gly Ser Cys Arg His Lys Gln
545                 550                 555                 560

Lys Ile Val Ala Pro Val Lys Gln Thr Leu Pro Pro Ser Asn Leu Arg
                565                 570                 575

Gly Asp Leu Gln Val Leu Ala Gln Lys Val Ala Arg Thr Leu Pro Cys
            580                 585                 590

Gly Asn Ser Val Asn Arg Met Leu Glu Lys Ala Ser Arg Lys His Gly
        595                 600                 605

Cys Ser Gln Ala Trp Leu Phe Trp Arg Met Arg Glu Asp Phe Gln Leu
```

-continued

```
              610              615              620
Asp Thr Asp
625

<210> SEQ ID NO 4
<211> LENGTH: 35
<212> TYPE: DNA
<213> ORGANISM: Artificial Sequence
<220> FEATURE:
<223> OTHER INFORMATION: Primer for amplification of P. aeruginosa
      OprI gene contained in plasmid pVUB3.

<400> SEQUENCE: 4
gcgcggatcc tgcagcagcc actccaaaga aaccg                                  35

<210> SEQ ID NO 5
<211> LENGTH: 32
<212> TYPE: DNA
<213> ORGANISM: Artificial Sequence
<220> FEATURE:
<223> OTHER INFORMATION: Primer for amplification of P. aeruginosa
      OprI gene contained in plasmid pVUB3.

<400> SEQUENCE: 5
ctttttcggt cggcgttcat tattcgaacg cg                                     32

<210> SEQ ID NO 6
<211> LENGTH: 8
<212> TYPE: PRT
<213> ORGANISM: Artificial Sequence
<220> FEATURE:
<223> OTHER INFORMATION: OVA-derived minimal CTL peptide.

<400> SEQUENCE: 6

Ser Ile Ile Asn Phe Glu Lys Leu
1               5
```